United States Patent
Saigal et al.

(10) Patent No.: US 11,607,383 B2
(45) Date of Patent: Mar. 21, 2023

(54) CONDUCTIVE POLYMER MICRONEEDLE ARRAYS FOR ELECTRONICALLY-CONTROLLED DRUG RELEASE

(71) Applicant: University of Washington, Seattle, WA (US)

(72) Inventors: Rajiv Saigal, Seattle, WA (US); Joyce Huang, Seattle, WA (US)

(73) Assignee: University of Washington, Seattle, WA (US)

( * ) Notice: Subject to any disclaimer, the term of this patent is extended or adjusted under 35 U.S.C. 154(b) by 193 days.

(21) Appl. No.: 17/069,587

(22) Filed: Oct. 13, 2020

(65) Prior Publication Data

US 2021/0106520 A1    Apr. 15, 2021

Related U.S. Application Data

(60) Provisional application No. 62/915,562, filed on Oct. 15, 2019.

(51) Int. Cl.
| | | |
|---|---|---|
| A61K 9/00 | (2006.01) | |
| A61K 47/34 | (2017.01) | |
| A61K 45/06 | (2006.01) | |

(52) U.S. Cl.
CPC .......... *A61K 9/0021* (2013.01); *A61K 9/0024* (2013.01); *A61K 9/0085* (2013.01); *A61K 9/0097* (2013.01); *A61K 47/34* (2013.01); *A61K 45/06* (2013.01)

(58) Field of Classification Search
None
See application file for complete search history.

(56) References Cited

U.S. PATENT DOCUMENTS

| 9,743,870 B2 | 8/2017 | Wang et al. |
| 2010/0074934 A1 | 3/2010 | Hunter |
| 2016/0038758 A1 | 2/2016 | Stahler et al. |
| 2017/0143967 A1 | 5/2017 | Blake, Jr. et al. |

FOREIGN PATENT DOCUMENTS

EP    1973479 B1    9/2016

OTHER PUBLICATIONS

Emam et al. Microsystem Technology 2008 14:371-378 (Year: 2008).*
Kwon et al. Journal of Microelectromechanical Systems 2014 23(6): 1274-1280 (Year: 2014).*
Bracken, M. et al. "Efficacy of Methylprednisolone in acute spinal cord injury," JAMA, 1984, 251, 45-52.
Bracken M. et al. "Administration of methylprednisolone for 24 or 48 hours or tirilazad mesylate for 48 hours in the treatment of acute spinal cord injury: results of the Third National Acute Spinal Cord Injury Randomized Controlled Trial," JAMA, 1997, 277(20), 1597-1604.
Huang, J. et al. "3D Printed Polypyrrole Microneedle Arrays for Electronically Controlled Drug Release," Society for Biomaterials Annual Meeting, Seattle, WA, Apr. 3-5, 2019.
Huang, J. "3D Printed Polypyrrole Microneedle Arrays for Electronically Controlled Drug Release," Bioengineering Capstone Presentation, University of Washington, Seattle, WA, May 20, 2019.
Hurlbert, R. J. et al. "Pharmacological therapy for acute spinal cord injury," Neurosurgery 76 Suppl 1, S71-83 (2015).
Li, J. et al. "Microneedle Patches as Drug and Vaccine Delivery Platform," Curr. Med. Chem. 24, 2413-2422 (2017).
Miller, P. et al. "Multiplexed Microneedle-based Biosensor Array for Characterization of Metabolic Acidosis," Talanta 88, 739-742 (2012).
Minev, I. et al. "Biomaterials. Electronic dura mater for long-term multimodal neural interfaces," Science, 347 (6218) 159-63.
National Spinal Cord Injury Statistical Center, "Spinal Cord Injury Facts and Figures at a Glance," Birmingham, AL: University of Alabama at Birmingham, 2018.
Schopla, N. et al. "Mitochondrial-based Therapeutics for the Treatment of Spinal Cord Injury: Mitochondrial Biogenesis as a Potential Pharmacological Target" Journal of Pharmacology and Experimental Therapeutics, 2017, 363(3), 303-313.
Tang-Schomer, M. et al. "Film Interface for Drug Testing for Delivery to Cells in Culture and in the Brain," Acta Biomaterialia vol. 94, 306-319.
Yeung, C. et al. "A 3D-printed microfluidic-enabled hollow microneedle architecture for transdermal drug delivery," Biomicrofluidics 13, 064125 (2019).
Gibbons, H. et al., "Microglia Induce Neural Cell Death Via a Proximity-Dependent Mechanism Involving Nitric Oxide," Brain Res 1084(1) (2006) 1-15.
Oyinbo, C., "Secondary Injury Mechanisms in Traumatic Spinal Cord Injury: A Nugget of this Multiply Cascade, Acta Neurobiol Exp" (Wars) 71(2) (2011) 281-99.
Donnelly, D. et al., "Inflammation and its role in neuroprotection, axonal regeneration and functional recovery after spinal cord injury," Exp Neurol 209(2) (2008) 378-88.
Park, E. et al., "The role of excitotoxicity in secondary mechanisms of spinal cord injury: a review with an emphasis on the implications for white matter degeneration," J Neurotrauma 21(6) (2004) 754-74.
Fehlings, M. et al., "The relationships among the severity of spinal cord injury, motor and somatosensory evoked potentials and spinal cord blood flow," Electroencephalogr Clin Neurophysiol 74(4) (1989) 241-59.

(Continued)

*Primary Examiner* — Melissa S Mercier
*Assistant Examiner* — Caralynne E Helm
(74) *Attorney, Agent, or Firm* — Christensen O'Connor Johnson Kindness PLLC

(57) ABSTRACT

The present disclosure describes a method of delivering a therapeutic agent providing a microneedle array including a plurality of microneedles, the plurality of microneedles including a conductive coating disposed thereon, wherein the conductive coating includes the therapeutic agent and a conducting polymer; implanting the microneedle array in a dura mater of a subject in need thereof, wherein the microneedle array pierces the dura mater; and applying an electrical stimulus to the microneedle array to provide a controlled release of the therapeutic agent from the conductive coating, across the dura mater, to the central nervous system of the subject.

9 Claims, 21 Drawing Sheets

(56) References Cited

OTHER PUBLICATIONS

Liu, X. et al., "Neuronal and glial apoptosis after traumatic spinal cord injury," J Neurosci 17(14) (1997) 5395-406.
Emery, E. et al., "Apoptosis after traumatic human spinal cord injury," J Neurosurg 89(6) (1998) 911-20.
Fehlings, M. et al., "Early versus delayed decompression for traumatic cervical spinal cord injury: results of the Surgical Timing in Acute Spinal Cord Injury Study (STASCIS)," PLoS One 7(2) (2012) e32037.
Walters, B. et al., "Guidelines for the Management of Acute Cervical Spine and Spinal Cord Injuries: 2013 update," Neurosurgery 60(CN_suppl_1) (2013) 82-91.
Gill, M. et al., "Neuromodulation of Lumbosacral Spinal Networks Enables Independent Stepping after Complete Paraplegia," Nature Medicine 24(11) (2018) 1677-1682.
Lavrov, I. et al., "Epidural Stimulation Induced Modulation of Spinal Locomotor Networks in Adult Spinal Rats," J Neurosci 28 (23) (2008) 6022-6029.
Zurita, M. et al., "Effects of Dexamethasone on Apoptosis-Related Cell Death After Spinal Cord Injury," J Neurosurg 96(1 Suppl) (2002) 83-9.
Kwon, B. et al., "Pathophysiology and Pharmacologic Treatment of Acute Spinal Cord Injury," Spine J 4(4) (2004) 451-64.
Bracken, M. et al., A Randomized, Controlled Trial of Methylprednisolone or Naloxone in the Treatment of Acute Spinal-Cord Injury, Results of the Second National Acute Spinal Cord Injury Study, N Engl J Med 322(20) (1990) 1405-11.
Hadley, M. et al., Pharmacological therapy after acute cervical spinal cord injury, Neurosurgery 50(3 Suppl) (2002) S63-72.
Baumann, M. et al., Intrathecal delivery of a polymeric nanocomposite hydrogel after spinal cord injury, Biomaterials 31(30) (2010) 7631-9.
Wilems, T. et al., Sustained dual drug delivery of anti-inhibitory molecules for treatment of spinal cord injury, J Control Release 213 (2015) 103-11.
Jain, A. et al., In situ gelling hydrogels for conformal repair of spinal cord defects, and local delivery of BDNF after spinal cord injury, Biomaterials 27(3) (2006) 497-504.
Perale, G. et al., "Multiple Drug Delivery Hydrogel System for Spinal Cord Injury Repair Strategies," J Control Release 159(2) (2012) 271-80.
Kim, Y. et al., "Nanoparticle-Mediated Local Delivery of Methylprednisolone after Spinal Cord Injury," Biomaterials 30(13) (2009) 2582-90.
Gupta, D. et al., "Fast-gelling Injectable Blend of Hyaluronan and Methylcellulose for Intrathecal, Localized Delivery to the Injured Spinal Cord," Biomaterials 27(11) (2006) 2370-9.
George, P. et al., "Fabrication and Biocompatibility of Polypyrrole Implants Suitable for Neural Prosthetics," Biomaterials 26(17) (2005) 3511-9.
Leprince, L. et al., "Dexamethasone Electrically Controlled Release from Polypyrrole-Coated Nanostructured Electrodes," J Mater Sci Mater Med 21(3) (2010) 925-30.
Wadhwa, R. et al., "Electrochemically Controlled Release of Dexamethasone from Conducting Polymer Polypyrrole Coated Electrode," J Control Release 110(3) (2006) 531-41.
Boehler C. et al., "Actively controlled release of Dexamethasone from Neural Microelectrodes in a Chronic in Vivo Study," Biomaterials 129 (2017) 176-187.
Gao, W. et al., "Action at a Distance: Functional Drug Delivery Using Electromagnetic-Field-Responsive Polypyrrole Nanowires," Langmuir 30(26) (2014) 7778-88.
Hui, B. et al., "Dexamethasone Sodium Phosphate Attenuates Lipopolysaccharide-Induced Neuroinflammation in Microglia BV2 Cells," Naunyn-Schmiedeberg's archives of pharmacology (2020).
Ogata, T. et al., "Steroid Hormones Protect Spinal Cord Neurons from Glutamate Toxicity," Neuroscience 55(2) (1993) 445-9.
Ridnour, L. et al., "A Spectrophotometric Method for the Direct Detection and Quantitation of Nitric Oxide, Nitrite, and Nitrate in Cell Culture Media," Analytical biochemistry 281(2) (2000).
Tan S. et al., "Inhibitory Effects of Palm α-, γ- And δ-Tocotrienol on Lipopolysaccharide-Induced Nitric Oxide Production in BV2 Microglia," Cellular immunology 271(2) (2011).
Ge, D. et al., "A Polypyrrole-Based Microchip for Controlled Drug Release," Electrochimica Acta 55(1) (2009) 271-275.
George, P. et al., "Electrically Controlled Drug Delivery from Biotin-Doped Conductive Polypyrrole," Advanced Materials 18(5) (2006) 577-581.
Cho, Y. et al., "A Mesoporous Silica Nanosphere-Based Drug Delivery System Using an Electrically Conducting Polymer, Nanotechnology" 20 (2009) 275102.
Huang, J., "3D Printed Polypyrrole Microneedle Arrays for Electronically Controlled Transdural Drug Release," University of Washington Bioengineering Thesis Defense, Seattle, Wa., Jun. 11, 2020.
"Stats About Paralysis—Prevalence of Paralysis in the United States," <http://www.christopherreeve.org/living-with-paralysis/stats-about-paralysis.com> [retreived Aug. 31, 2020], 7 pages.

* cited by examiner

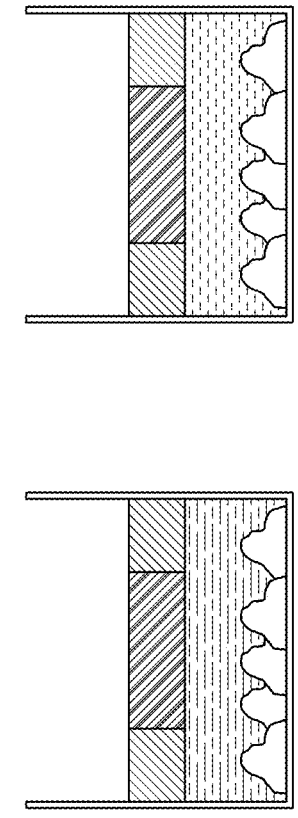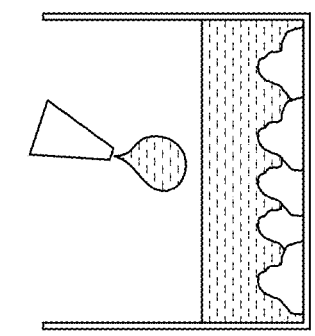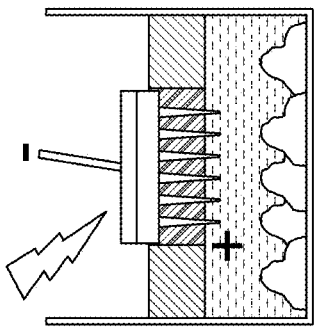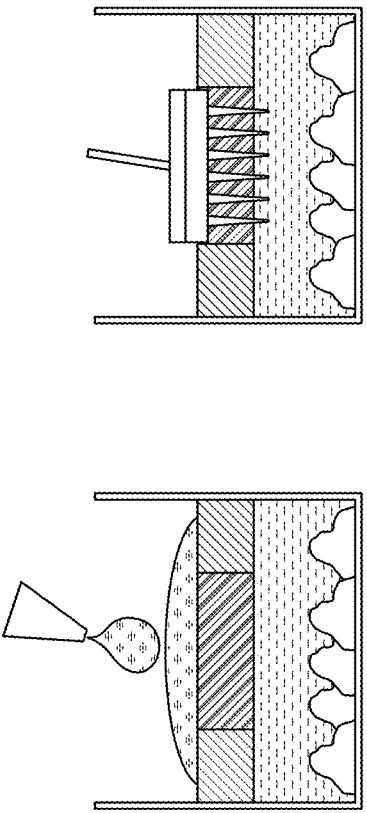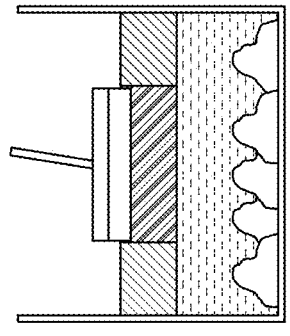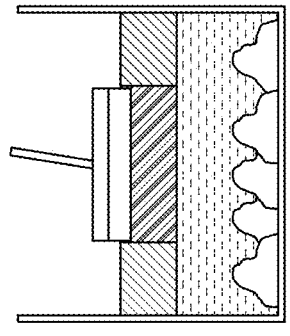
FIG. 5A  FIG. 5B  FIG. 5C  FIG. 5D  FIG. 5E  FIG. 5F  FIG. 5G

CONDUCTIVE POLYMER MICRONEEDLE ARRAYS FOR ELECTRONICALLY-CONTROLLED DRUG RELEASE

CROSS-REFERENCES TO RELATED APPLICATIONS

This application claims the benefit of Provisional Application No. 62/915,562, filed Oct. 15, 2019, the entire disclosure of which is hereby incorporated by reference herein for all purposes.

BACKGROUND

Currently in the United States, approximately 288,000 people live with spinal cord injuries, and approximately 17,700 new cases of spinal cord injuries occur per year. Of the new cases, less than 1% make a complete recovery by hospital discharge. Spinal cord and traumatic brain injuries (SCI and TBI, respectively) can result in secondary injury causing further damage to neural cells, due to mechanisms of inflammation and cytotoxicity. Activation of microglia due to the injuries causes the release of inflammation factors and free radicals, which lead to the death of surrounding neurons. Secondary injury mechanisms of neuroinflammation, excitotoxicity, and ischemia attribute to further damage of the injured spinal cord. For example, excitotoxicity caused by excess neurotransmitters, free radicals, reactive oxygen species, released as a result of the primary injury, lead to deaths of surrounding uninjured cells. Released inflammatory factors stimulate inflammatory responses of surrounding glial cells, resulting in the release of proapoptotic factors and additional free radicals. Free radicals such as nitric oxide (NO) released by inflammatory microglia have been found to damage surrounding uninjured tissue. Excessive NO induce apoptosis in nearby neurons. This secondary apoptotic neuron death has been observed at a distance from the injury site, for up to several weeks post-injury.

Current treatments for spinal cord and brain injuries can include surgery and physical therapy. Investigated treatments include the use of steroids for their anti-inflammatory and neuroprotective properties, the most common of which is methylprednisolone. Clinical trials of systemic methylprednisolone showed higher recovery of motor functions in treatment groups. However, its use is controversial and some have advocated against it because of lack of efficacy and systemic side effects. At the systemic dosage required to show benefit, evidence also shows the results of serious side effects, including pulmonary embolism and sepsis. Due to the lack of other pharmacological solutions that show a similar benefit, the use of methylprednisolone remains a treatment option. Additionally, dural opening (durotomy) for implantation can increase the risk of cerebral spinal fluid leak, as well as that of infection; thus, it would be beneficial to minimize opening of the dura for drug delivery.

The use of controlled local delivery may reduce side effects and improve efficacy. Local delivery may reduce off-target effects, while maintaining local concentration. Local controlled release also has the added benefit of allowing therapeutic agents to be delivered without need to cross the blood-brain barrier. Many promising therapeutic agents, particularly large molecule and protein therapeutics, are restricted by their inability to cross the blood-brain barrier that surrounds the spinal cord. These therapeutic agents are thus restricted to single bolus delivery through dural punctures. These restrictions have prompted the development of certain intrathecal and intramedullary local controlled release therapies. However, the use of these systems require incisions of the dura (e.g., using a surgical blade), the protective sheath that encases the cerebrospinal fluid (CSF) and the spinal cord. This approach of opening the dura adds risk of CSF leak, meningitis, and damage to the spinal cord itself. Thus, dural incisions should be avoided if possible.

There is a need for a therapeutic delivery system that can deliver therapeutic agents locally into the intrathecal space, without the need for durotomy and with minimal damage to the dura, while not impeding neural functions. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a method of delivering a therapeutic agent to a central nervous system, including: providing a microneedle array including a plurality of microneedles, the plurality of microneedles including a conductive coating disposed thereon, wherein the conductive coating includes the therapeutic agent and a conducting polymer; implanting the microneedle array in a dura mater of a subject in need thereof, wherein the microneedle array pierces the dura mater; and applying an electrical stimulus to the microneedle array to provide a controlled release of the therapeutic agent from the conductive coating, across the dura mater, to the central nervous system of the subject.

In another aspect, the present disclosure features an implantable microneedle array, including: a plurality of microneedles including a conductive coating disposed thereon, wherein the conductive coating includes a therapeutic agent and a conducting polymer; the implantable microneedle array is configured to be implanted in a dura mater and the microneedle array is configured to pierce a dura mater; and the microneedle array controllably releases the therapeutic agent from the conductive coating upon application of an electrical stimulus.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 5A is a schematic representation of in vitro neuroinflammation experimental conditions: unactivated BV2 microglia.

FIG. 5B is a schematic representation of in vitro neuroinflammation experimental conditions: activated BV2 microglia without treatment.

FIG. 5C is a schematic representation of in vitro neuroinflammation experimental conditions: subdural therapeutic agent (dexamethasone, "Dexa") solution treatment of activated microglia.

FIG. 5D is a schematic representation of in vitro neuroinflammation experimental conditions: electrically stimulated conductive (polypyrrole, "PPy") microneedles (with therapeutic agent (Dexa) or blank).

FIG. 5E is a schematic representation of in vitro neuroinflammation experimental conditions: epidural therapeutic agent solution.

FIG. 5F is a schematic representation of in vitro neuroinflammation experimental conditions: non-stimulated microneedles with therapeutic agent (Dexa) and conducting polymer (PPy).

FIG. 5G is a schematic representation of in vitro neuroinflammation experimental conditions: stimulated flat conducting polymer (PPy) release.

DETAILED DESCRIPTION

Figures 1A, 1B:
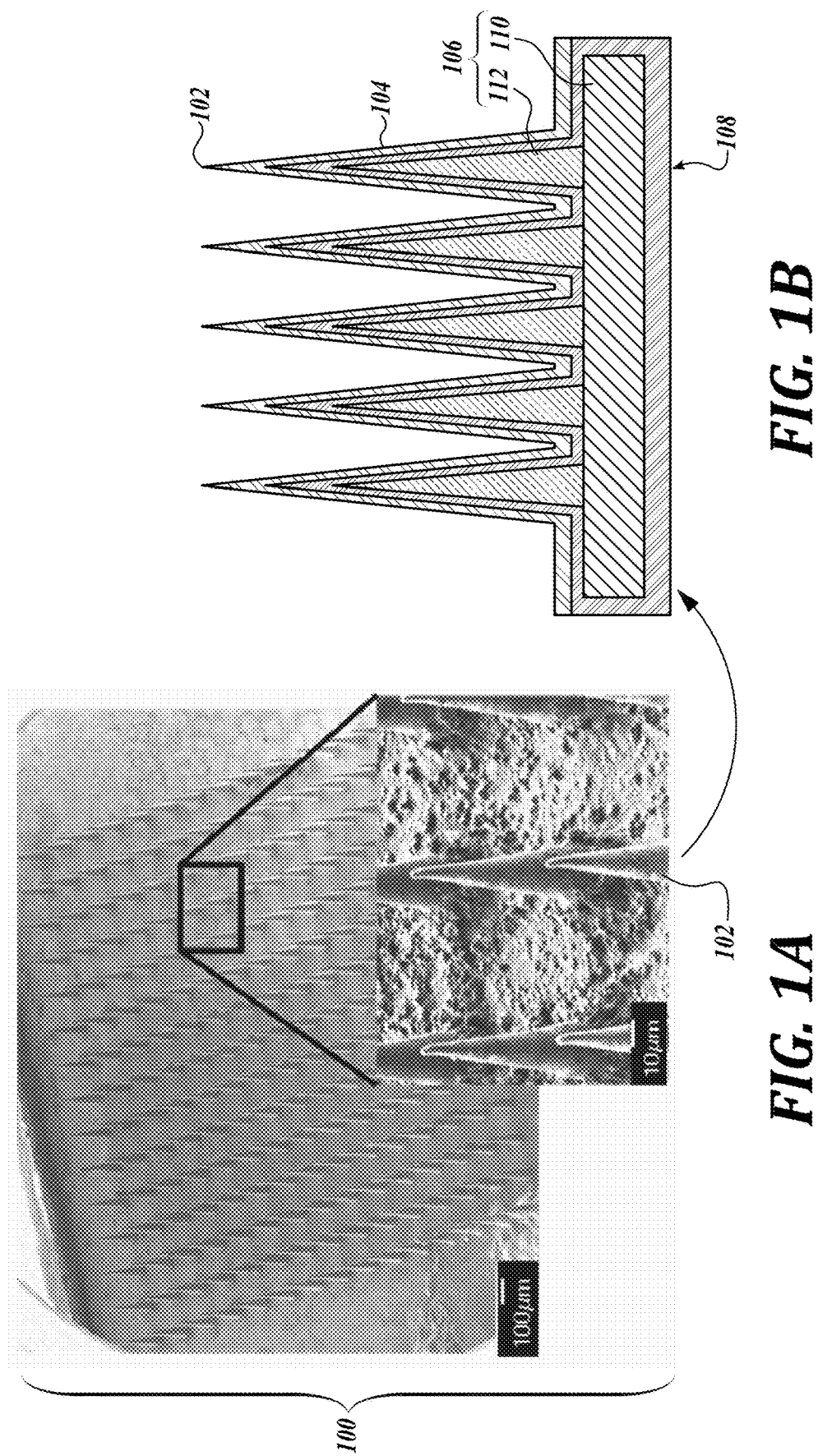
FIG. 1A is a microscopic image of an embodiment of a microneedle array of the present disclosure.
FIG. 1B is a cross-sectional view of an embodiment of a microneedle array of the present disclosure.

The present disclosure describes a method of delivering a therapeutic agent to a central nervous system, including:

providing a microneedle array including a plurality of microneedles, the plurality of microneedles including a conductive coating disposed thereon, wherein the conductive coating includes the therapeutic agent and a conducting polymer; implanting the microneedle array in a dura mater of a subject in need thereof, wherein the microneedle array pierces the dura mater; and applying an electrical stimulus to the microneedle array to provide a controlled release of the therapeutic agent from the conductive coating, across the dura mater, to the central nervous system of the subject.

The present disclosure also describes an implantable microneedle array, including: a plurality of microneedles including a conductive coating disposed thereon, wherein the conductive coating includes a therapeutic agent and a conducting polymer; the implantable microneedle array is configured to be implanted in a dura mater and the microneedle array is configured to pierce a dura mater; and the microneedle array controllably releases the therapeutic agent from the conductive coating upon application of an electrical stimulus.

The transdural delivery method provides electronically controlled delivery from the conducting polymer across the dura mater, while minimizing or eliminating the need for surgical incisions into the dura. The implanted microneedle array then allows the local delivery of therapeutic agents across the dura mater to the central nervous system of the subject. The microneedle array can be implanted into the subject, for example, during a decompression surgery. In some embodiments, the implant can be placed epidurally, while piercing the dura to deliver drugs to the intrathecal space.

The delivery method and microneedle array lowers systemic dosage and reduces risks of durotomy. As the therapeutic agent delivery using the microneedles is localized, higher dosage of therapeutic agent can be administered. Microneedles are inserted transdurally for therapeutic agent release without the need for aggressive durotomy.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "aryl" refers to monocyclic or polycyclic (e.g., having 2, 3, or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms.

As used herein, the term "halo" or "halogen" includes fluoro, chloro, bromo, and iodo.

As used herein, "heteroalkyl" refers to an alkyl group having at least one heteroatom such as sulfur, oxygen, or nitrogen.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, a "monomeric unit" refers to a group of atoms, derived from a molecule of a given monomer, that includes a constitutional unit of a polymer or a macromolecule.

As used herein, a monomer refers to a molecule which can undergo polymerization thereby contributing constitutional units to the essential structure of a macromolecule. As used herein, when a monomer forms part of a polymer chain, it is understood that the monomer refers to a monomeric unit.

As used herein, "polymer" is a molecule composed of at least 2 repeating structural units typically connected by covalent chemical bonds. The repeating structural unit may be one type of monomeric unit, and the resulting polymer is a homopolymer. In some embodiments, the polymers can include two different types of monomeric units, or three different types of monomeric units, or more types of monomeric units, to result in a heteropolymer. One of ordinary skill in the art will appreciate that the different types of monomeric units can be distributed along a polymer chain in a variety of ways. For example, three different types of monomeric units can be randomly distributed along the polymer. It will similarly be appreciated that the distribution of monomeric units along the polymer can be represented in different ways. The number of repeating structural units (e.g., monomeric units) along the length of a polymer can be represented by "n." In some embodiments, n can range, e.g., from at least 2, from at least 100, from at least 500, from at least 1000, from at least 5000, or from at least 10,000, or from at least 100,000, or higher. In certain embodiments, n can range from 2 to 10000, from 20 to 10000, from 20 to 500, from 50 to 300, from 100 to 1000, or from 500 to 10,000.

Polymers generally have extended molecular structures including backbones that optionally contain pendant side groups. The polymers provided herein can include, but are not limited to, linear polymers and branched polymers such as star polymers, comb polymers, brush polymers, ladders, and dendrimers. As described further herein, the polymers can include semiconducting polymers generally well known in the art.

The polymer can, e.g., be a "conjugated polymer" or a "conducting polymer." The terms "conjugated polymer" and "conducting polymer" are recognized in the art. Electrons, holes, or electronic energy, can be conducted along the conjugated structure. In some embodiments, a large portion of the polymer backbone can be conjugated. In some embodiments, the entire polymer backbone can be conjugated. In some embodiments, the polymer can include conjugated structures in their side chains or termini. In some embodiments, the conducting polymer conducts electricity. In some embodiments, the conducting polymer can have semiconducting properties, e.g., the polymers can exhibit a direct band gap, leading to an efficient absorption or emission at the band edge.

As used herein, the term "random copolymer" is a copolymer having an uncontrolled mixture of two or more constitutional units. The distribution of the constitutional units throughout a polymer backbone can be a statistical distribution, or approach a statistical distribution, of the constitutional units. In some embodiments, the distribution of one or more of the constitutional units is favored. For a polymer made via a controlled polymerization (e.g., RAFT, ATRP, ionic polymerization), a gradient can occur in the polymer chain, where the beginning of the polymer chain (in the direction of growth) can be relatively rich in a constitutional unit formed from a more reactive monomer while the later part of the polymer can be relatively rich in a constitutional unit formed from a less reactive monomer, as the more reactive monomer is depleted. To decrease differences in distribution of the constitutional units, comonomers in the same family (e.g., methacrylate-methacrylate, acrylamide-acrylamido) can be used in the polymerization process, such that the monomer reactivity ratios are similar.

As used herein, the term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —$CH_2CH_2O$— corresponding to a repeat unit, or —$CH_2CH_2OH$ corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

Compounds of the disclosure can also include all isotopes of atoms occurring in the intermediates or final compounds. Isotopes include those atoms having the same atomic number but different mass numbers. For example, isotopes of hydrogen include tritium and deuterium.

As used herein, "biocompatible" refers to a property of a molecule characterized by it being not, or at least minimally and/or reparably, injurious to living tissue; and/or not, or at least minimally and controllably, causing an immunological reaction in living tissue. As used herein, "physiologically acceptable" is interchangeable with biocompatible.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of a therapeutic agent (i.e., drug, or therapeutic agent composition) that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be readily understood that the aspects of the present disclosure, as generally described herein, and illustrated in the FIGURES, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an example embodiment may include elements that are not illustrated in the FIGURES. As used herein, with respect to measurements, "about" means+/−5%. As used herein, a recited range includes the end points, such that from 0.5 mole percent to 99.5 mole percent includes both 0.5 mole percent and 99.5 mole percent.

Controlled Delivery Methods

As discussed above, the present disclosure describes a method of delivering a therapeutic agent to a central nervous system, including providing a microneedle array including a plurality of microneedles, the plurality of microneedles including a conductive coating disposed thereon, wherein the conductive coating includes the therapeutic agent and a conducting polymer; implanting the microneedle array in a dura mater of a subject in need thereof, wherein the microneedle array pierces the dura mater; and applying an electrical stimulus to the microneedle array to provide a controlled release of the therapeutic agent (e.g., a therapeutically effective amount of the therapeutic agent) from the conductive coating, across the dura mater, to the central nervous system of the subject.

In some embodiments, the microneedle array is implanted epidurally by a neurosurgeon at the time of brain or spine surgery. The microneedle array is placed in the epidural space and then the microneedles puncture the dura to allow delivery of drug to the subdural, intrathecal, and/or intramedullary space. The electrodes can be connected to a power source or implanted controller that delivers the necessary voltage or current for drug release.

In some embodiments, suitable patients is any patient undergoing brain or spine surgery, especially one who may benefit from a locally delivered therapeutic agent, as can be determined by a person of skill in the art. In some embodiments, a suitable patient is a neurotrauma patient (e.g., TBI or SCI), cancer patient, epilepsy patient, Parkinson's patient, and the like.

In some embodiments, the electrical stimulus includes application of a voltage of from −10 V to 10 V (e.g., from −5 V to 5 V, from −7 V to 7 V or from −1 V to 1 V) for a duration of from 1 second to 72 hours (e.g., from 1 minute to 24 hours, from 4 minutes to 12 hours, from 4 minutes to 6 hours, or from 5 minutes to 30 minutes) to the microneedle array. IN some embodiments, the electrical stimulus includes application of a voltage of from −5 V to 5 V for a duration of from 1 minute to 24 hours (e.g., 5 minutes to 30 minutes) to the microneedle array. In a preferred embodiment, the electrical stimulus includes application of a voltage of from −1 V to 1 V for a duration of from 5 minutes to 30 minutes to the microneedle array. In some embodiments, when the electrical stimulus includes an increased voltage, the electrical stimulus can be applied for a shorter duration. Without wishing to be bound by theory, it is believed that when the electrical stimulus is applied, the conducting polymer backbone is reduced and the therapeutic drug(s) are then released.

In some embodiments, the electrical stimulus is cycled. The cycling can occur, for example, at a rate of from 80 mV/second to 120 mV/second (e.g., about 100 mV/second).

In some embodiments, the microneedle array is implanted in a dura mater that is located in a spinal cord of the subject. In certain embodiments, the microneedle array is implanted in a dura mater that is located in a brain of the subject.

In some embodiments, the microneedle array is adapted to deliver the therapeutic agent epidurally, transdurally, subdurally, and/or intraparenchymally. As used herein, "epidurally" refers a therapeutic agent that is delivered superficially to the dura. As used herein, "transdurally" refers to a penetration of the microneedles into the dura from the epidural side and delivery of the therapeutic agent subdurally or deeper. As used herein, "subdurally" refers to a deep delivery of the therapeutic agent into the dura. As used herein, "intraparenchymally" refers to the therapeutic agent delivery to the inside of the spinal cord or brain. In certain embodiments, the method consists essentially of, or consists of, implanting the microneedle array in a dura mater of a subject in need thereof, such that the microneedle array pierces the dura mater; and applying an electrical stimulus to the microneedle array to provide a controlled release of the therapeutic agent from the conductive coating, across the dura mater, to a select organ, such as the central nervous system of the subject.

Delivery System

Referring to FIG. 1A, the implantable microneedle array 100 of the present disclosure can includes a plurality of microneedles 102. Referring to FIG. 1B, the plurality of microneedles 102 include a conductive coating 104 disposed thereon, the conductive coating includes a therapeutic agent and a conducting polymer. The implantable microneedle array is configured to be implanted in a dura mater and the microneedle array is configured to pierce the dura mater. The microneedle array controllably releases the therapeutic agent from the conductive coating upon application of an electrical stimulus to the microneedle array.

The microneedle array can be flexible, such that the microneedle array substrate can conform to the movements and contours of the dura mater when implanted into a subject.

In some embodiments, the microneedle array can be coupled (e.g., electrically coupled) to a control unit, such as a remote controller (e.g., via electrodes), such that the remote controller can provide on-demand application of the electrical stimulus to release the therapeutic agent from the conductive coating. In some embodiments, the microneedle array further include an electrical stimulus source connected to the microneedle array via one or more electrodes. The electrical stimulus source can be, for example, a battery. In some embodiments, the battery can be implanted into the subject together with the microneedle array.

In some embodiments, the conducting polymer has a conducting backbone that is a polypyrrole, polythiophene, polyaniline, poly(3,4-ethylenedioxythiophene), or substituted derivatives thereof. The conducting polymer can have a molecular weight $M_W$ of 500 or more (e.g., 1,000 or more, 2,500 or more, 5,000 or more, or 10,000 or more) and/or 15,000 or less (e.g., 10,000 or less, 5,000 or less, 2,500 or less, or 1,000 or less). In some embodiments, the conducting polymer can be substituted, for example, with alkyl, heteroalkyl, haloalkyl, aryl, heteroaryl, halo, amino, alkylamino, or dialkylamino substituents. The substituents can be directly bonded to the backbone of the conducting polymer, or bonded to a side chain pendant on the conducting polymer.

In some embodiments, the therapeutic agent is an anti-inflammatory agent, a serotonin agonist, a neurotrophic factor, or any combination thereof. In some embodiments, the therapeutic agent is dexamethasone, methylprednisolone, triamcinolone, IL-10, quipazine, riluzole, a nerve growth factor, a brain-derived neurotrophic factor, a neuroregenerative agent (e.g., a NOGO antibody, a rho inhibitor), a neuroprotective agent, a chemotherapeutic agent, a bone-growth stimulating agent, a pharmaceutically acceptable prodrug thereof, a pharmaceutically acceptable salt thereof, or any combination thereof. For example, the therapeutic agent can be dexamethasone, methylprednisolone, IL-10, quipazine, riluzole, a nerve growth factor, a brain-derived neurotrophic factor, a pharmaceutically acceptable prodrug thereof, a pharmaceutically acceptable salt thereof, or any combination thereof. In some embodiments, the therapeutic agent is dexamethasone, methylprednisolone, a pharmaceutically acceptable prodrug thereof, a pharmaceutically acceptable salt thereof, or any combination thereof. In some embodiments, the therapeutic agent is a surface negative agent (e.g., anionic). In certain embodiments, when the therapeutic agent is neutral or positively charged, the therapeutic agent can be encapsulated (e.g., in a micelle, in a particle, or in a vesicle) or otherwise modified to be surface negative.

In some embodiments, referring again to FIG. 1, the microneedle array 100 includes a substrate 106, a metal layer 108 over the substrate 106, and the conductive coating 104 over the metal layer 108. As used herein, the substrate includes the support structure on which a metal layer (e.g., gold layer) and the conductive coating (e.g., the conducting polymer and the therapeutic agent) are deposited. For example, the substrate can include a platform 110 having thereon the microneedle scaffold structures 112 on which the metal layer and the conductive coating will be deposited.

In some embodiments, at least a portion of microneedles of the plurality of microneedles is solid. In some embodiments, the microneedles of the array are not hollow and/or do not include a channel in the microneedles that can contain, for example, the therapeutic agent.

In some embodiments, the therapeutic agent is dispersed in the conducting polymer. The therapeutic agent can be homogeneously dispersed, or can be dispersed in the conducting polymer in discrete regions. In some embodiments, the therapeutic agent is dissolved in a solution of the conducting polymer before application onto the substrate. In some embodiments, the therapeutic agent is dissolved in a solution of a monomer for the conducting polymer, and the therapeutic agent is deposited concurrently as the deposition of the resulting conducting polymer, which is polymerized in situ during the deposition process.

In some embodiments, the therapeutic agent is in the form of a layer, and the conducting polymer is a discrete layer that overlays the layer of therapeutic agent, such that the conducting polymer layer is positioned above (e.g., immediately above and contacting) the layer of therapeutic agent.

In some embodiments, at least a portion of microneedles of the plurality of microneedles has a height of from 100 µm to 3000 µm (e.g., from 100 µm to 500 µm, from 500 µm to 1000 µm, from 500 µm to 2000 µm, or from 1000 µm to 3000 µm) and a base diameter of from 25 µm to 500 µm (e.g., from 25 µm to 50 µm, from 25 µm to 300 µm, from 50 µm to 100 µm, or from 100 µm to 500 µm). In a preferred embodiment, least a portion of microneedles of the plurality of microneedles has a height of from 500 µm to 2000 µm and a base diameter of from 25 µm to 300 µm. The microneedles can form a point at the tip to facilitate piercing of the dura mater during implantation. At least a portion of microneedles of the plurality of microneedles can bend upon application of a force on the tip of the microneedles, and the shape of the microneedles can recover upon removal of the force. In some embodiments, the microneedles can have a x-y plane (z-axis refers to the height of the microneedles) cross section that is circular, rectangular, hexagonal, triangular, pentagonal, and/or star-shaped.

Method of Making the Microneedle Array

Figure 2:
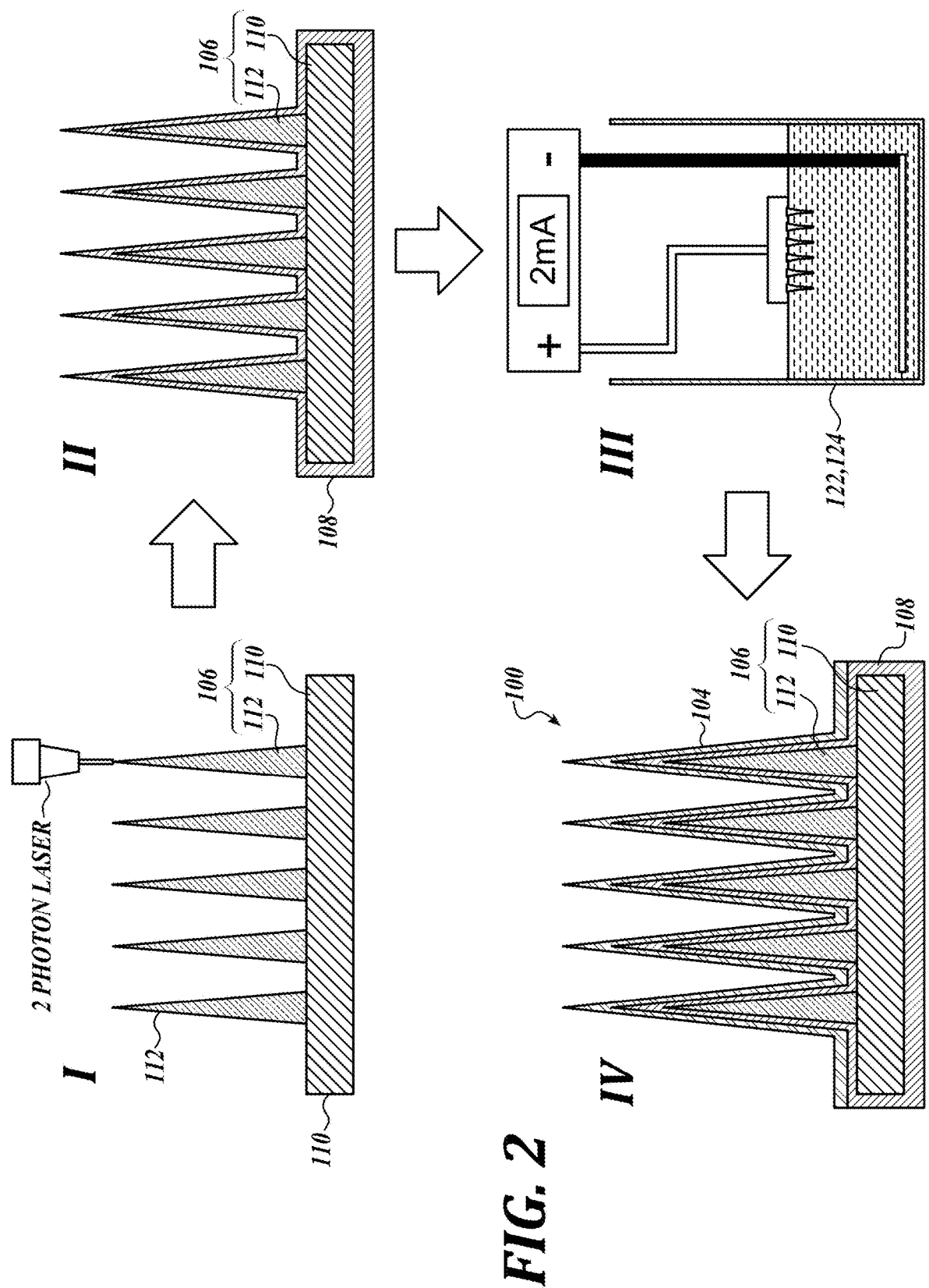
FIG. 2 is a schematic representation of a method of making an embodiment of a microneedle array of the present disclosure.

The microneedle array of the present disclosure can be made according to any process known to a person of ordinary skill in the art. For example, referring to FIG. 2, the microneedle array can be made by providing a platform 110, such as a silicon or a polymeric platform having a flat surface, 3D-printing a microneedle array scaffold 112 (e.g., using IP-S, or using a photolithographic process) onto the platform to provide a substrate 106 in step I, sputter coating a conducting metal (e.g., gold) layer 108 onto the microneedle scaffold in step II, and applying a coating of a therapeutic agent 122 with a monomer 124 that is polymerized in situ to provide a conducting polymer, or a layer of therapeutic agent followed by a layer of a conducting polymer, either in the form of a monomer that is polymerized in situ or in the form of a pre-formed conducting polymer, onto the conducting metal layer 108 in step III to provide a microneedle array shown in step IV. The conductive coating of a therapeutic agent and a conducting polymer can be deposited on the metal layer by electrodeposition, electropolymerization, or and chemical oxidation-reduction.

In some embodiments, a conducting polymer adhesion layer is first deposited on the conducting metal layer before deposition of the conductive coating. The conducting polymer adhesion layer can have a thickness of from tens of nm (e.g., 10 nm, 20 nm, 30 nm, 40 nm, 50 nm, 60 nm, 80 nm, or 100 nm) to hundreds of µm (e.g., 100 µm, 200 µm, 500 µm, or 750 µm).

The following Examples describe the formation and characterization of microneedle arrays for controlled release of therapeutic agents.

EXAMPLE

Example 1. Microneedle Array for Transdural Drug Delivery

A conducting polymer microneedle array that includes a drug which can be released on demand via an electronic control is described below. A polypyrrole (PPy) microneedle array was prepared using micro-scale 3D printing technology that allows electronically-controlled encapsulation and controlled release of drugs. The anti-inflammatory capabilities of the device were tested by electronic release of dexamethasone (Dexa), an anti-inflammatory drug, into an in vitro model of activated BV2 microglia cells. After 72 hours of incubation, nitric oxide (NO) production and inflammatory cytokine release from the cells were quantified. In vitro studies showed that application of dexamethasone through stimulated release from the device reduced both nitric oxide production and IL1-b, an inflammatory cytokine. The transdural drug delivery ability of the PPy microneedles was tested through an in vitro transdural model. The PPy microneedles were able to deliver drug across the dural substitute. These results demonstrate that PPy microneedles, and other conducting polymer microneedles, can be used for transdural delivery of anti-inflammatory drugs.

The delivery system lowers systemic dosage and reduces risks of durotomy. Anti-inflammatory therapeutic agents, such as dexamethasone, delivered via such system, reduced neuroinflammation. The therapeutic agent was released upon electronic stimulation. As the drug delivery using the microneedles is localized, higher dosage of therapeutic agent can be administered. Microneedles are inserted transdurally for therapeutic agent release without the need for aggressive durotomy.

Microneedle Fabrication

Figure 3:
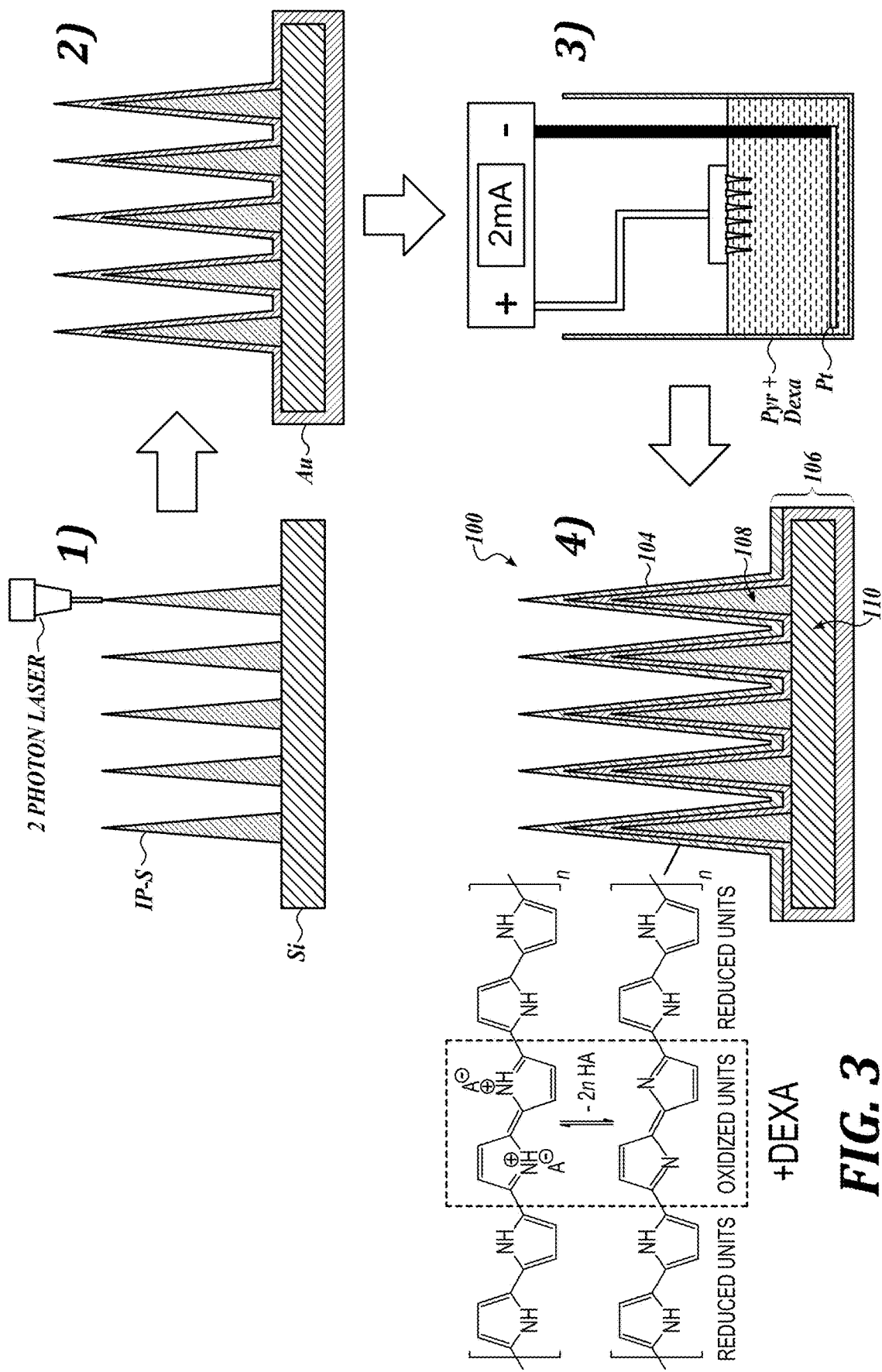
FIG. 3 is a schematic representation of a method of making an embodiment of a microneedle array of the present disclosure. Step 1 shows a 3D photolithography of microneedles on silicon substrate; Step 2 shows sputter coating of the microneedle surface with a conducting metal (gold); Step 3 shows an electrodeposition of a therapeutic agent and conducting polymer on a microneedle substrate surface using a pyrrole and dexamethasone solution; and Step 4 shows a cross section of completed PPy microneedles.

Referring to FIG. 3, microneedles were fabricated using three-dimensional photolithography (NanoScribe GnbH, NanoScribe). 10×10 arrays of conical microneedles with 500 μm height and 130 μm diameter, along with a 20 μm thick square base, were printed on plasma-treated silicon wafers in IP-S resist (NanoScribe) as shown in FIG. 3, step 1. Microneedles in the array were spaced at every 250 μm from point-to-point. Exposed microneedles were then developed in SU-8 Developer (Microchem) for 20 minutes, followed by cleaning in an isopropanol solution for 5 minutes. Following developing, microneedles were further cured under a UV flood light (ABM) of approximately intensity 11.5 lx for 90 seconds. Microneedle wafers were then diced into 7 mm×7 mm chips each containing an individual microneedle array. In Step 2, microneedle chips were coated on both surfaces by sputter coating (Evatec LLS EVO Sputter System) in 10 nm chrome and 100 nm gold. The sputtered coating was allowed to coat the sides, and forming electrical connections between the top and bottom surfaces. Electrical connections were made by soldering to the surface opposite the microneedles. The metal-coated microneedle electrodes were then deposited in PPy following the protocol below. Flat electrodes were made similarly through dicing and sputter coating silicon, followed by soldering and Dexa PPy electrodeposition.

PPy Deposition

Microneedle electrodes to be coated in PPy were submerged in a solution of 0.2M pyrrole monomer (Pyr, ThermoFisher) and 0.2M sodium dodecylbenzenesulfonate (NaDBS, ThermoFisher) in water across a platinum anode. A blank (no drug) adhesion layer was first deposited by the application of 1 mA across the Pyr solution for 2 minutes. The electrode was then submerged in a Pyr solution for the treatment layer, and subjected to 2 mA of current for 4 minutes. Referring to Step 3 in FIG. 3, treatment layer for the blank PPy was again deposited in fresh 0.2M Pyr, 0.2M NaDBS solution. Treatment layer of the Dexamethasone PPy (Dexa PPy) was deposited in a solution of 0.2M Pyr, 100 mg/ml dexamethasone phosphate (Dexa), without NaDBS to provide the microneedle array shown in Step 4. Excess and unbound Pyr monomers and dopants were then removed by washing in 0.9M phosphate buffered saline (PBS, Gibco) three times on a rotating shaker for five minutes each.

Microneedle Array Mechanical Characterization

The mechanical strength of the fabricated microneedles was tested using an in situ indentor (Alemnis) under SEM (Thermofisher Apreo S). The microneedles were indented using a stainless-steel flat punch tip. Indentation of the microneedles occurred at 17.3 nm/sec until 10 μm total displacement. Microneedles were then also indented at 75 nm/sec until 20 μm, 150 nm/sec until 35 μm, and 500 nm/sec until 35 μm. New microneedles were used for each indentation. Resultant load at each displacement point was recorded.

In Vitro Transdural Release

Figure 4A:
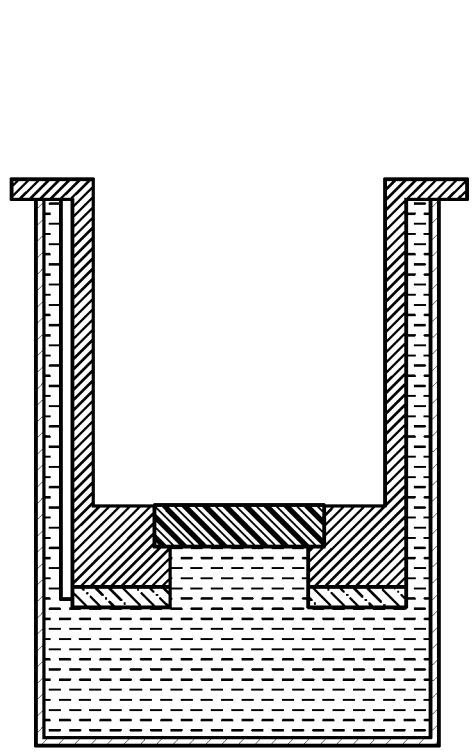
FIG. 4A is a schematic representation of an embodiment of a transdural model in solution. Artificial dura is suspended over solution in 3D printed polylactic acid (PLA) transwell insert.
Figure 4B:
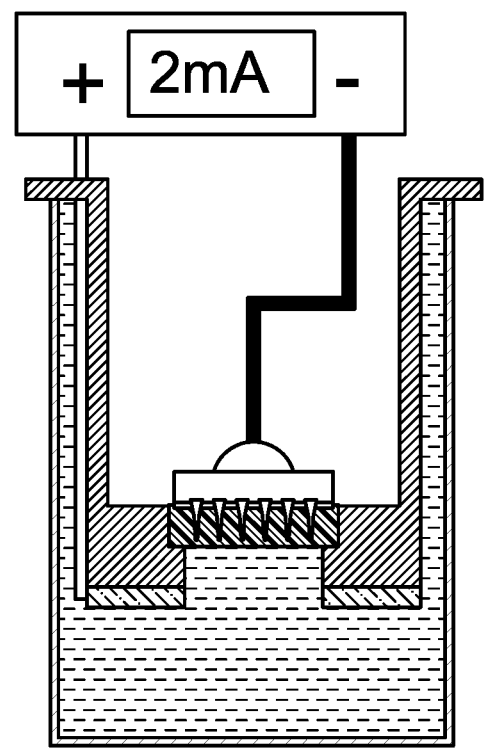
FIG. 4B is a schematic representation of an embodiment of microneedle application to the transdural model shown in FIG. 4A. The bottom surface of the insert was coated in gold to form a conductive surface for electrical stimulation through the solution. Microneedles were applied to the insert epidurally.
Figure 4C:
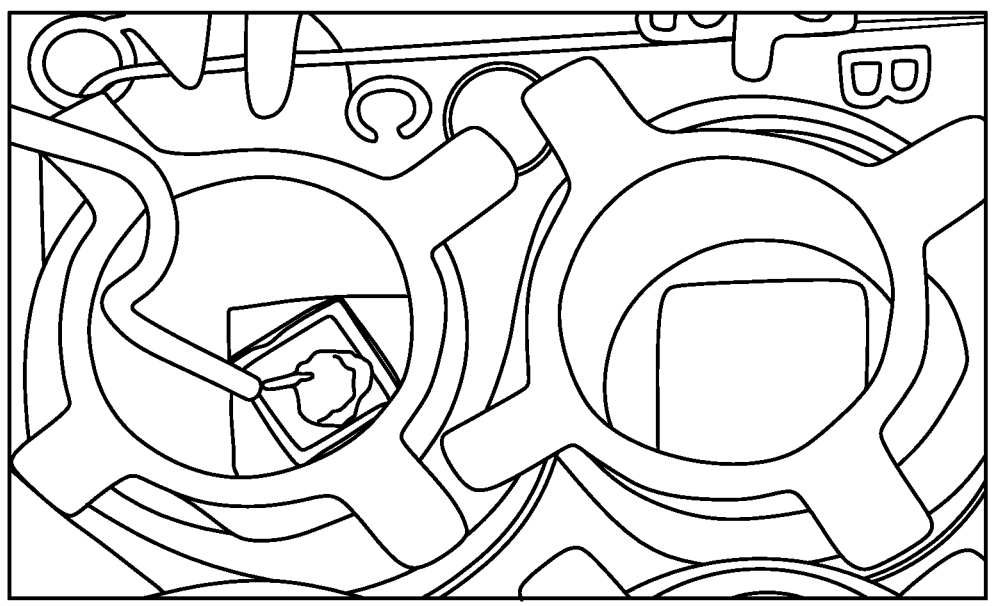
FIG. 4C is a photograph of an embodiment of a microneedle array in the in vitro transdural model of FIGS. 4A and 4B.

Transdural release assays from the PPy microneedles, as well as controls, were performed in a custom transwell in vitro model shown in FIGS. 4A-4C. Transwell inserts were designed and 3D printed in polylactic acid (PLA) to allow suspension of a dural substitute (DuraMatrix) over solution within a 12 well plate. The bottom and outside surfaces of the insert were sputter coated in 10 nm of chrome and 100 nm of gold to create a counter-electrode for stimulated release. A square of suturable dura substitute was then fixed to bottom opening of the transwell insert using cyanoacrylate gel (Loctite). The fixed transdural insert was then allowed to dry, then the dura hydrated with 400 μl of PBS. Transdural inserts were placed into wells over 1.6 ml of PBS. Microneedles were applied epidurally over the dura substitute using manual pressure. Flat electrodes were placed and stimulated similarly.

Electrical stimulation was then be applied through the microneedle to the coated insert as an electrode (FIG. 4B). Stimulated release samples underwent 10 minutes of direct current (DC) at −2V or cyclic voltammetry (CV) of 100 mV/s from −1V to 1V. Groups of n=6 microneedle arrays were stimulated under DC for 10 minutes in order to allow quantification of maximum release. However, due to apparent cell stress and death from long durations of DC stimulation, the DC stimulated release was also performed at a reduced duration of 2 minutes. Drug in solution were applied to epidural and subdural controls by pipetting over or below the dural insert, respectively. 200 μl of Dexa solution with a concentration of 50 ug/ml was used in controls.

An SEM image of the microneedles was taken before and after the transdural placement. To allow for SEM imaging, electrical connections to the microneedle array were removed, thus microneedles imaged immediately after PPy deposition were not subsequently used for implantation and transdural release. Another microneedle array was used for transdural implantation and release was similarly processed and imaged in SEM.

Dexamethasone Quantification

Dexa phosphate (Dexa) released was quantified using high pressure liquid chromatography (HPLC) and mass spectrometry (MS). Prednisolone phosphate (Pred) was added to each sample as an internal standard, prior to processing. Each sample received prednisolone phosphate to a final sample concentration of 2 μg/ml. Drug release samples were passed through a 0.2 μm PVDF filter prior to autosampler injection. Aqueous and organic phases used were 10 mM ammonium acetate in water and methanol, respectively. The compounds were separated in chromatography through a Zorbax Extend C-18 3.5 μm HPLC column (Agilent), at a flow rate of 0.3 mL/min Dexa and Pred ions of m/z 471.1500 and 439.1043, respectively, were extracted. The Pred ion was isolated with a peak at approximately 2.00 minutes (mins), and the Dexa ion at approximately 3.75 mins. For each compound, fragments of m/z 79 and 97 were isolated in negative ion mode, and used for quantification. Dexa in the solution was quantified by comparison against a calibration curve of Dexa in PBS, with similarly added Pred. Samples were quantified using the ratio of Dexa to the constant concentration of internal standard Pred.

In Vitro Neuroinflammation Assay

Bioactivity of electrically released drug was tested in an in vitro neuroinflammation model, in which drugs were released into wells of activated BV2 murine microglia. Healthy BV2 cells were seeded in 12-well plates at a density of 100,000 cells/well, in 1.6 mL of Dulbecco's modified eagle media (DMEM, Gibco) with 4.5 g/L D-glucose, 584 mg/L L-glutamine, and 110 mg/L sodium pyruvate (Invitrogen). The DMEM was supplemented with 5% fetal bovine serum (Invitrogen) and 2% anti-mycotic/anti-biotic (Invitrogen). Following seeding, the cells were incubated at 37° C. overnight to allow for settling and adhesion. Cells in activated treatment groups were activated by the replacement of media with fresh DMEM containing 0.005% interferon gamma (Ifn-γ, Invitrogen) and 1% lipopolysaccharide (LPS, ThermoFisher). Unactivated controls received normal fresh DMEM. Cells were then incubated for 1 hour before application of treatment in groups of n=6, in order to simulate realistic conditions in which there is a duration between traumatic SCI occurrence and access to treatment.

Treatment was applied transdurally from microneedles into the cell media though the transdural insert model as previously described in the In Vitro Transdural Release section. Diagrams of experimental conditions can be found in FIGS. 5A-5G. Microneedles were similarly applied manually, then underwent a potentiostatic or cyclic electrical stimulation. Direct current potential was applied for only 2 minutes to minimize electrical imbalance applied to the cells, while delivering sufficient drug to achieve therapeutic effect. Cyclic voltammetry was applied for 15 cycles, equating to 10 minutes. Epidural drug solution controls were similarly applied to the neuroinflammation model by pipetting over the transdural insert. In addition, a subdural solution control was introduced to the neuroinflammation studies in which the Dexa solution is applied directly to the cell media, bypassing the transdural insert.

Following 3 days of incubation, cell media was assayed for markers of inflammation. Free radical nitric oxide (NO) was quantified using a Griess reagent kit (Invitrogen) that detects NO reduced to nitrites in cell medias. Colorimetric NO quantification was performed following the protocols provided in the Griess reagent kit. Pro-inflammatory cytokines were quantified using a Luminex Magpix Multiplexing assay (Millipore). Cytokines quantified include interleukin-1-beta (IL-1β), interleukin-6 (IL-6), and tumor necrosis factor alpha (TNF-α). Cells treated in the CV stimulated experiment were additionally quantified for the release of monocyte chemoattractant protein 1 (MCP-1). The Luminex multiplexing assays were performed following the protocol provided in the kit.

Cell viability was measured using an MTS assay (Cell-Titer 96® AQueous One Solution Cell Proliferation Assay, Promega). Cells received 1 ml of fresh DMEM, along with 200 μl of MTS reagent, then were incubated for 1 hour. The incubation was followed by detection of absorbance at 490 nm. The MTS absorbance in each group was normalized to the absorbance of the unactivated group.

Statistical Analysis

Statistical analysis was performed using SPSS Statistics 25 (IBM). Sample groups were checked for normal distribution using a Shapiro-wilk test, then checked for homogeneity of variances using Leven's test. One-way ANOVA with post-hoc Bonferroni analysis was performed on experiments with 3 or more groups, and homogeneity of variances. Experiments without homogeneity of variances were instead assessed using a post-hoc Games-Howell test. Student's T test was performed on experiments with 2 groups.

Results and Discussion

Microneedle Mechanical Characterization

Figure 6:
FIG. 6 is a SEM micrograph of an embodiment of a microneedle of the present disclosure under compression stress testing.

To characterize the mechanical strength of the microneedles, the microneedles were subjected to stress testing under a nanoindenter. The microneedles were compressed in the indenter under a constant rate of displacement, while visualized using SEM. Under SEM visualization, it was apparent that the microneedles experienced bending rather than compression under the force of the indenter (FIG. 6). Due to bending and change in contact surface area, the mechanical strength of the microneedle could not be determined.

However, load vs displacement curves allowed qualitative assessment of the elasticity of the microneedles. On application of downward force, the tip of the microneedle bends, but recovers as the force is removed. The magnitude of plastic deformation is dependent on the rate of displacement. The magnitude of deformation increased as the rate of displacement was increased. The difference in deformation can be seen in displacement rates of 150 nm/sec and 500 nm/sec both to a maximum of 35 μm. With a load of max displacement 20 μm and greater, the point of bending was seen at approximately 4 μm, where the rapid increase in load is reduced as the tip is bent.

In Vitro Transdural Drug Release

Figure 7:
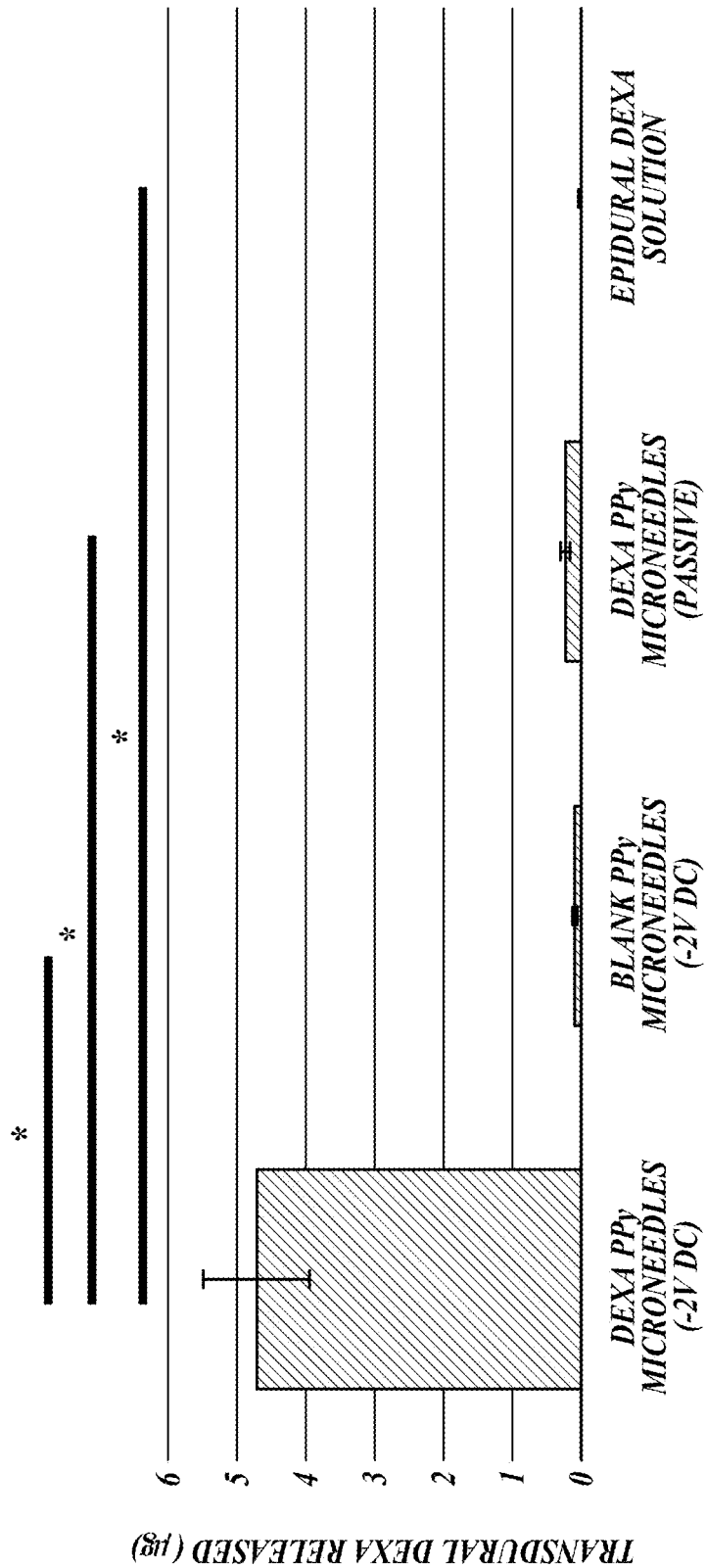
FIG. 7 is a bar graph showing quantified transdural release from a direct current (DC) stimulation of an embodiment of a microneedle array of the present disclosure, where the conductive coating includes a therapeutic agent and conducting polymer (dexamethasone (Dexa) and polypyrrole (PPy)). The bar graph shows a mass of Dexa in subdural solution following transdural release using DC stimulated microneedles including therapeutic agent and conducting polymer, DC stimulated blank microneedles with conducting polymer but no therapeutic agent, non-stimulated (Passive Dexa PPy microneedles), and epidural Dexa stimulation. (* $p<0.05$).

Drug release from 10×10 arrays of Dexa PPy microneedles was tested in a custom designed in vitro model to demonstrate transdural release. In this model, the microneedles were used to puncture artificial dura at the bottom of a transwell insert, and released into solution below. Electrical stimulation can then be applied through the solution. In addition, transdural release was tested in microneedles without electrical stimulation, as well as microneedles without drug, and from epidurally applied Dexa solution (FIG. 7). As expected, PPy microneedles without drug did not result in subdural Dexa release. Similarly, epidural Dexa solution resulted in no subdural Dexa, indicating that Dexa released epidurally does not undergo passive diffusion through the transdural insert. Quantification of subdural solution found that Dexa PPy microneedles that experience 10 minutes of −2V potentiostatic stimulation resulted in a significantly higher amount of transdural Dexa release. The use of Dexa PPy microneedles appears to allow transdural release of Dexa. Similar Dexa PPy microneedles without electrical stimulation resulted in very little transdural Dexa release, illustrating electrical control of Dexa release from Dexa PPy microneedles. The ability for electrically stimulated release allowed for precise temporal control of drug release, with external control throughout duration of implantation. Along with local implantation for transdural release, the DexaPPy microneedles demonstrated the capability for temporal and spatial control of drug delivery to the spinal cord.

Figure 8:
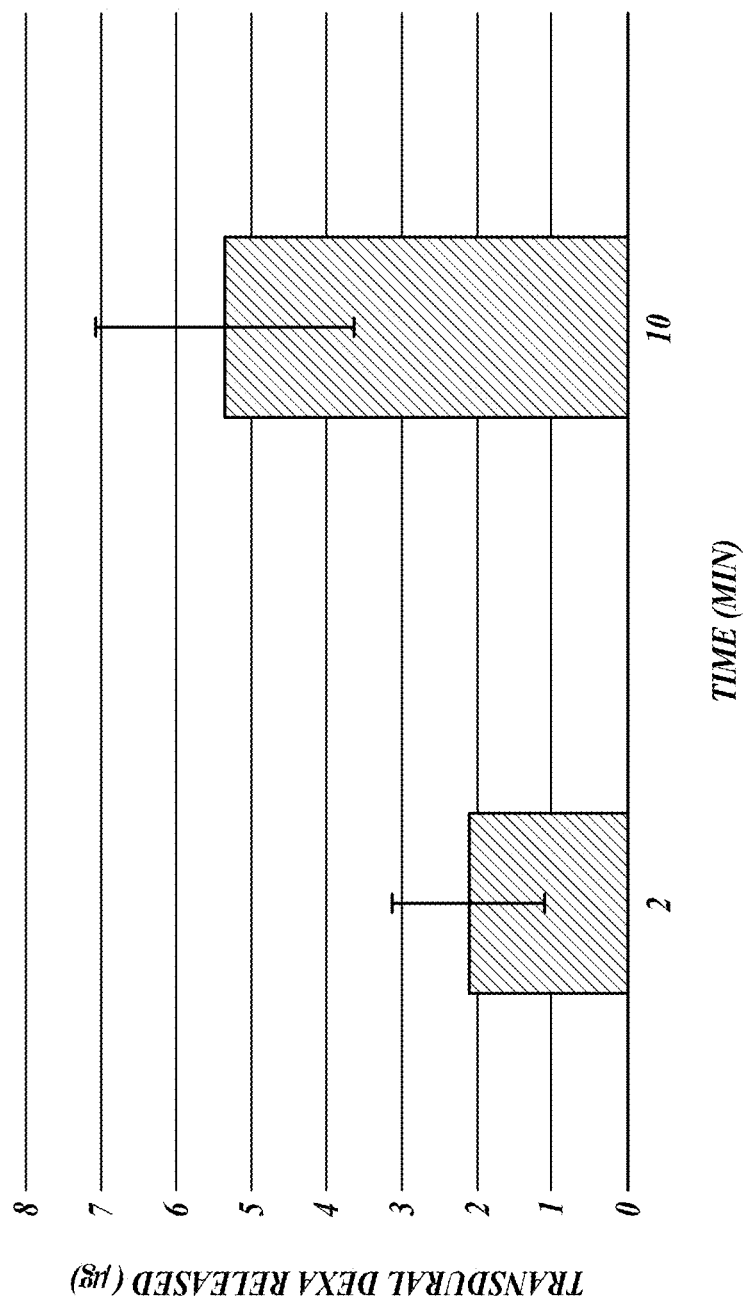
FIG. 8 is a bar graph showing a quantified transdural therapeutic agent release from DC stimulation of an embodiment of a microneedle array of the present disclosure, at 2 minutes and 10 minutes.

To adapt the release process to a cellular neuroinflammation model, the duration of stimulation can be reduced, for example, to 2 minutes. Transdural drug release from the Dexa PPy microneedles with 2 minutes of electrical stimulation was similarly quantified in the in vitro model. Reduced duration electrical stimulation resulted in lower amounts of drug release (FIG. 8). The decreased stimulation reduced transdural drug release by approximately 60% to a total of 2 μg.

Figure 9:
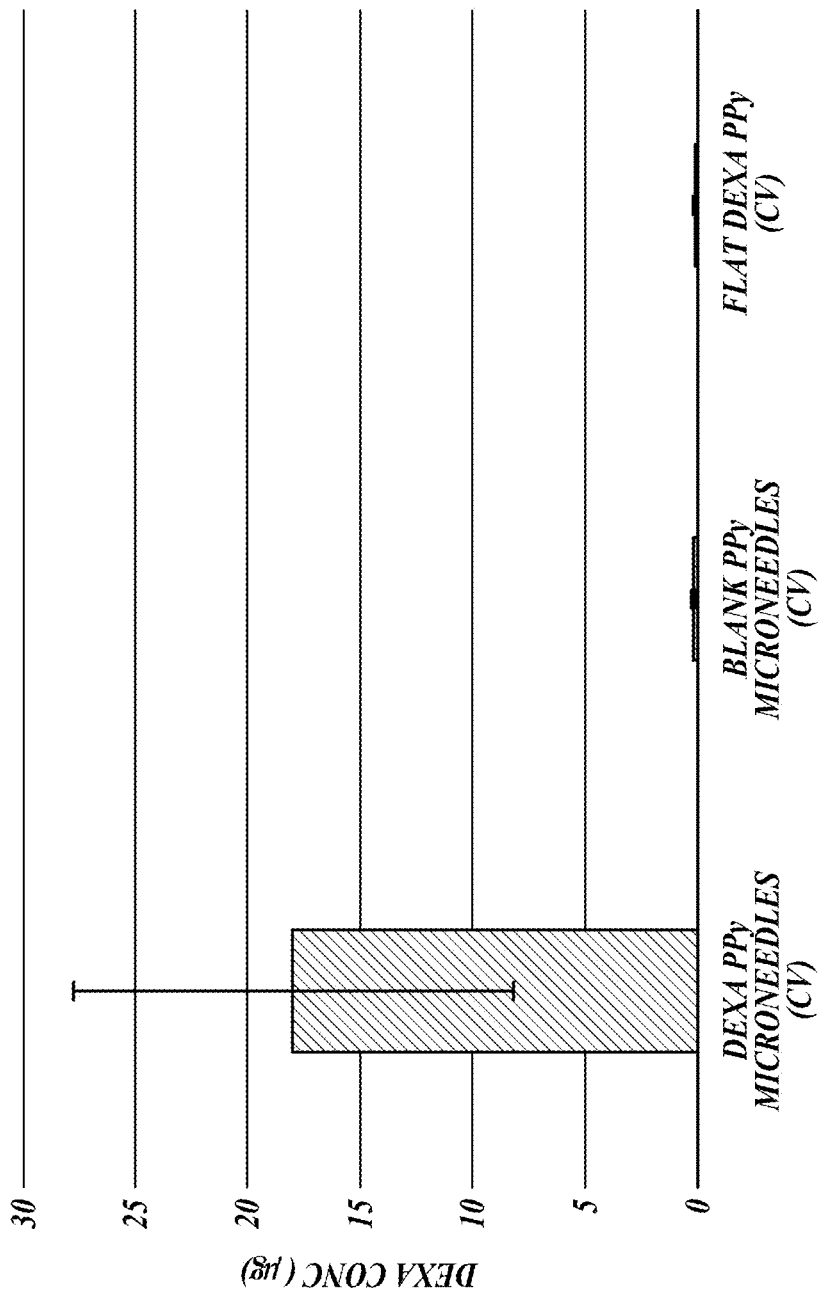
FIG. 9 is a bar graph showing a subdural therapeutic agent release from cyclic voltammetric (CV) stimulation of an embodiment of a microneedle array of the present disclosure. The bar graph shows subdural therapeutic agent quantification following transdural release from CV stimulation of microneedles including therapeutic agent and conducting polymer, blank microneedles with conducting polymer but no therapeutic agent, and flat microneedles with therapeutic agent and conducting polymer.

Stimulation of the DexaPPy microneedles was also studied using cyclic voltammetry to reduce over-oxidation of the PPy, and allow for charge balancing when stimulating in a cellular environment. The drug release was similarly performed in the in vitro transdural model. A cyclic potential of 100 mV/s from −1V to 1V was applied. The CV stimulation was applied for 15 cycles, equating to 10 minutes of stimulation. The peak current throughout the CV stimulation remained level, indicating a lack of over-oxidation seen in long duration DC stimulation. The ability to maintain PPy conductivity suggests that CV stimulation may be applied for durations extending beyond 15 cycles, for higher amounts of drug release. Ten minutes of CV stimulated release from Dexa PPy microneedles resulted in an average of 18.03 μg of transdural Dexa release (FIG. 9). The CV stimulated Dexa release was variable. The variability may be attributed to variable release from PPy. Nevertheless, all but one sample achieved a minimum of 3 µg Dexa release.

Flat DexaPPy electrodes and Blank PPy microneedles were also tested for transdural release with CV stimulation. Neither resulted in measurable transdural Dexa release. The lack of transdural Dexa release from Flat Dexa PPy with stimulation demonstrated the inability of Dexa to cross the transdural well through electrical forces alone. The lack of electrically-driven transdural release indicates that microneedles play a role in allowing Dexa to cross the membrane.

Figure 10A:
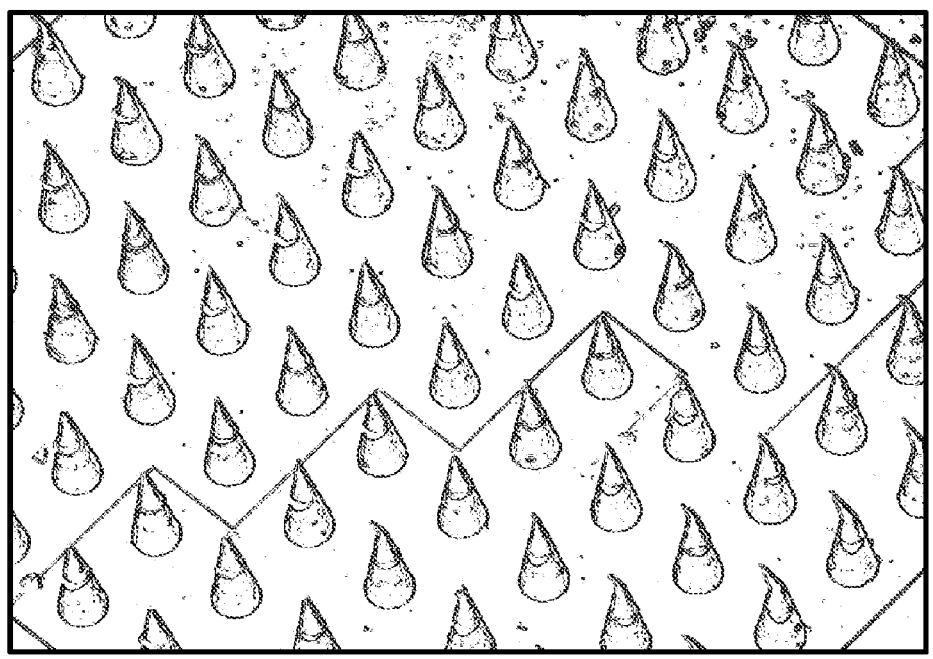
FIG. 10A is a SEM image of an embodiment of a microneedle array of the present disclosure prior to implantation into a transdural insert. The microneedles in the array have 500 μm height and 130 μm base diameter.
Figure 10B:
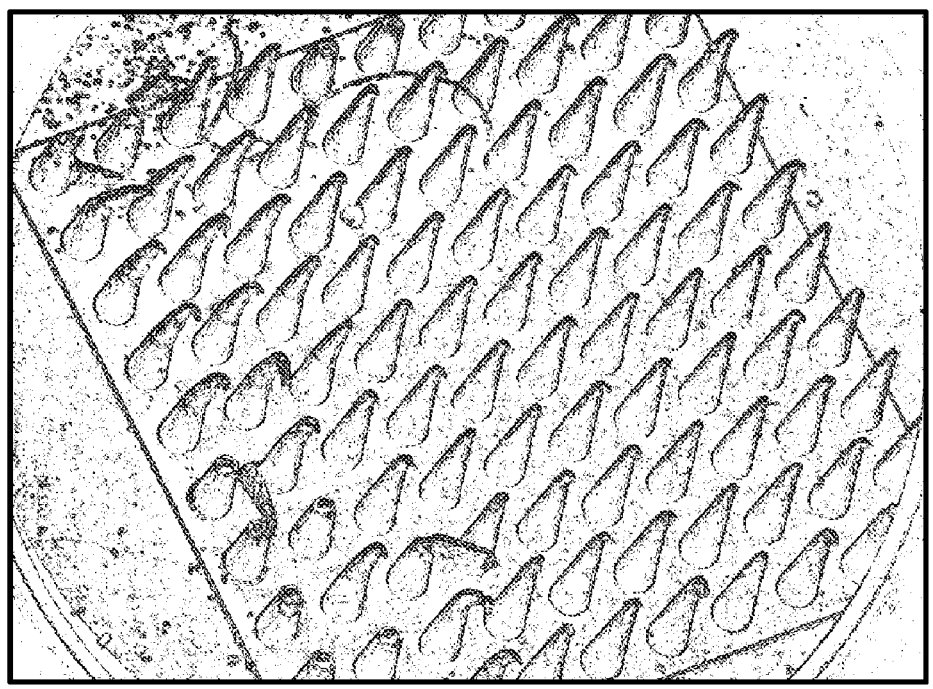
FIG. 10B is a SEM image of an embodiment of a microneedle array of the present disclosure after implantation into a transdural insert. The microneedles in the array have 500 μm height and 130 μm base diameter.

SEM imaging of the microneedles before and after implantation into the dura insert demonstrated the durability of the microneedles against the artificial dura membrane (FIGS. 10A and 10B). Representative SEM images were taken of a microneedle array following PPy deposition. While some microneedles experience slight bending prior to implantation, most display a sharp peak. Following implantation, microneedles experience some blunting, as well as slight hooking of the tip, however, most microneedles maintained structural integrity through implantation and drug release.

In Vitro Neuroinflammation Assay

DC Stimulated Release

Transdural Dexa release from the microneedles was similarly tested in a neuroinflammation assay in vitro. BV2 Microglia cells were cultured in the wells of the transdural release model, and activated for inflammation using Ifn-γ and LPS. Shortly following activation, the cells received treatment. Cells were treated with subdural Dexa solution, DC stimulated Dexa PPy microneedles, epidural Dexa solution, non-stimulated Dexa PPy microneedles, and DC stimulated blank PPy microneedles. Additional control groups of unactivated cells, and activated but untreated cells were also included. After three days of incubation, the cells are assayed for NO release, inflammatory cytokine release, and cell viability. The release of NO and cytokines were normalized to the quantified cell viability in order to account for cell death or changes in rate of proliferation resultant of the treatments.

Figure 11A:
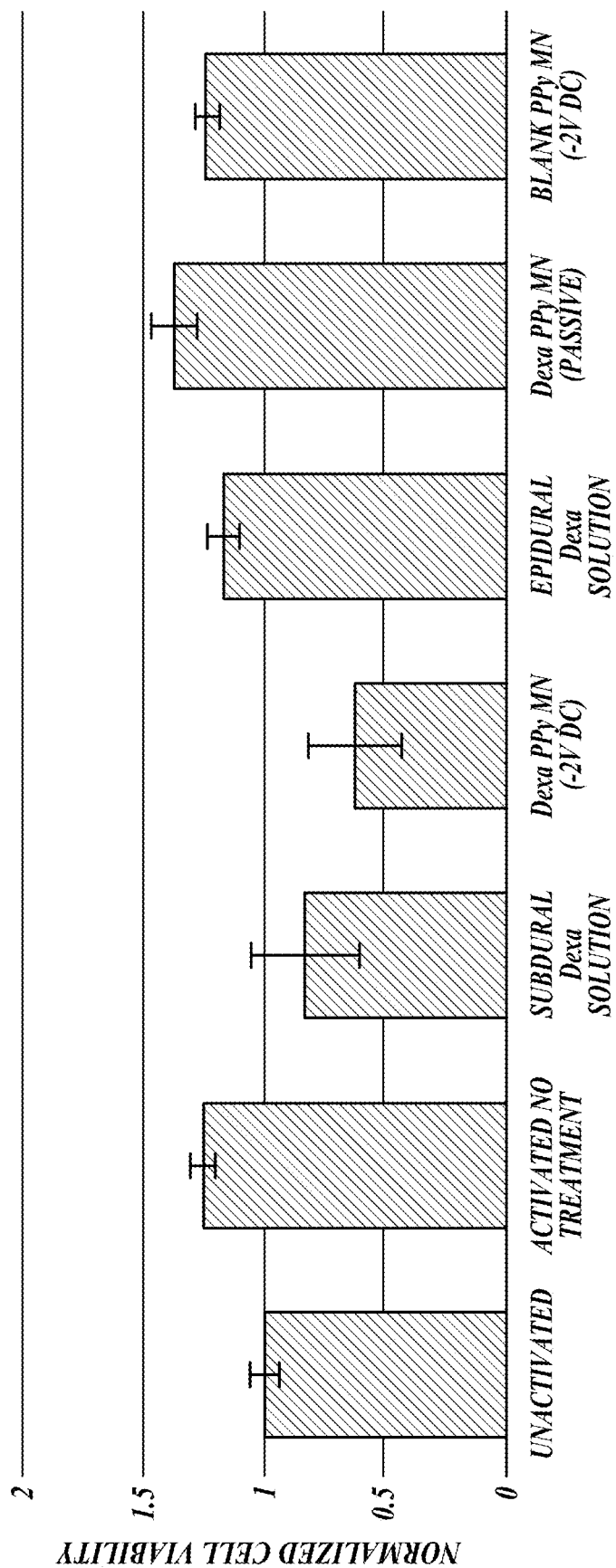
FIG. 11A is a bar graph of a neuroinflammation assay following transdural treatment that includes DC stimulation of an embodiment of a microneedle array of the present disclosure: normalized cell viability as quantified using MTS colorimetric MTS metabolism.

The relative cell viability of the treated cells was quantified using an MTS assay. The MTS assay is used for indirect quantified cell viability by measuring the metabolism of the MTS compound by mitochondrial dehydrogenases. On analysis of cell viability (FIG. 11A), it was noted that the group treated with DC stimulated Dexa PPy microneedles saw a significant decrease in cell viability. The subdural Dexa group saw slight decreases in viability, though not significant. The decrease in metabolism of MTS may indicate a decrease in proliferation rate in Dexa treated cells.

Figure 11B:
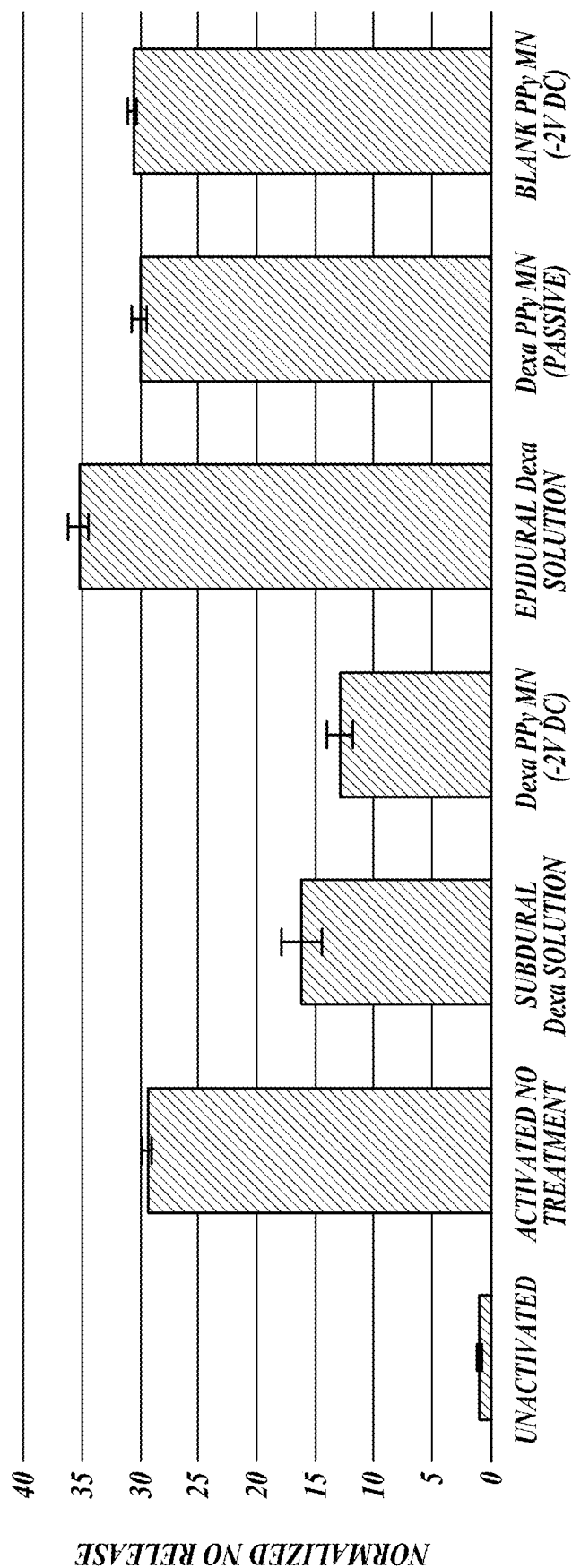
FIG. 11B is a bar graph of a neuroinflammation assay following transdural treatment that includes DC stimulation of an embodiment of a microneedle array of the present disclosure: release of NO normalized by the amount of viable cells quantified by MTS metabolism.

The relative cell viability results were used to normalize the release of free radical NO and pro-inflammatory cytokines IL-1β, IL-6, and TNF-α. Normalized NO (FIG. 11B) saw a significant decrease in cells treated with subdural Dexa solution, demonstrating decrease of NO in Dexa treated microglia. Cells treated with DC stimulated Dexa PPy microneedles experienced a similar decrease in NO release, through electrically stimulated transdural release of Dexa. Groups of epidural Dexa solution, passive release from Dexa PPy microneedles, and DC stimulated Blank PPy microneedles did not demonstrate the same decrease. These results correspond with previous transdural release quantification, in which only stimulated Dexa PPy microneedles resulted in transdural Dexa release.

Figure 11C:
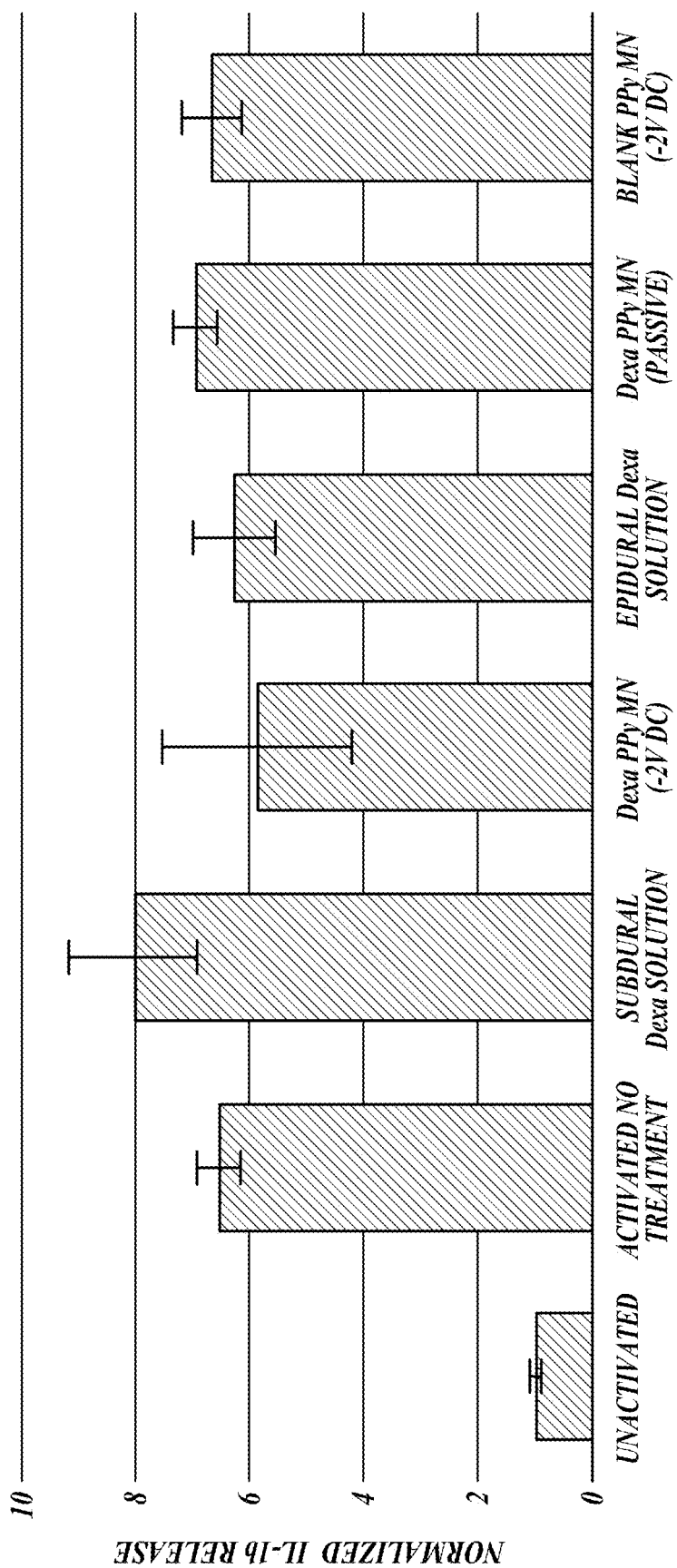
FIG. 11C is a bar graph of a neuroinflammation assay following transdural treatment that includes DC stimulation of an embodiment of a microneedle array of the present disclosure: IL-1β release normalized by the amount of viable cells quantified by MTS metabolism.
Figure 11D:
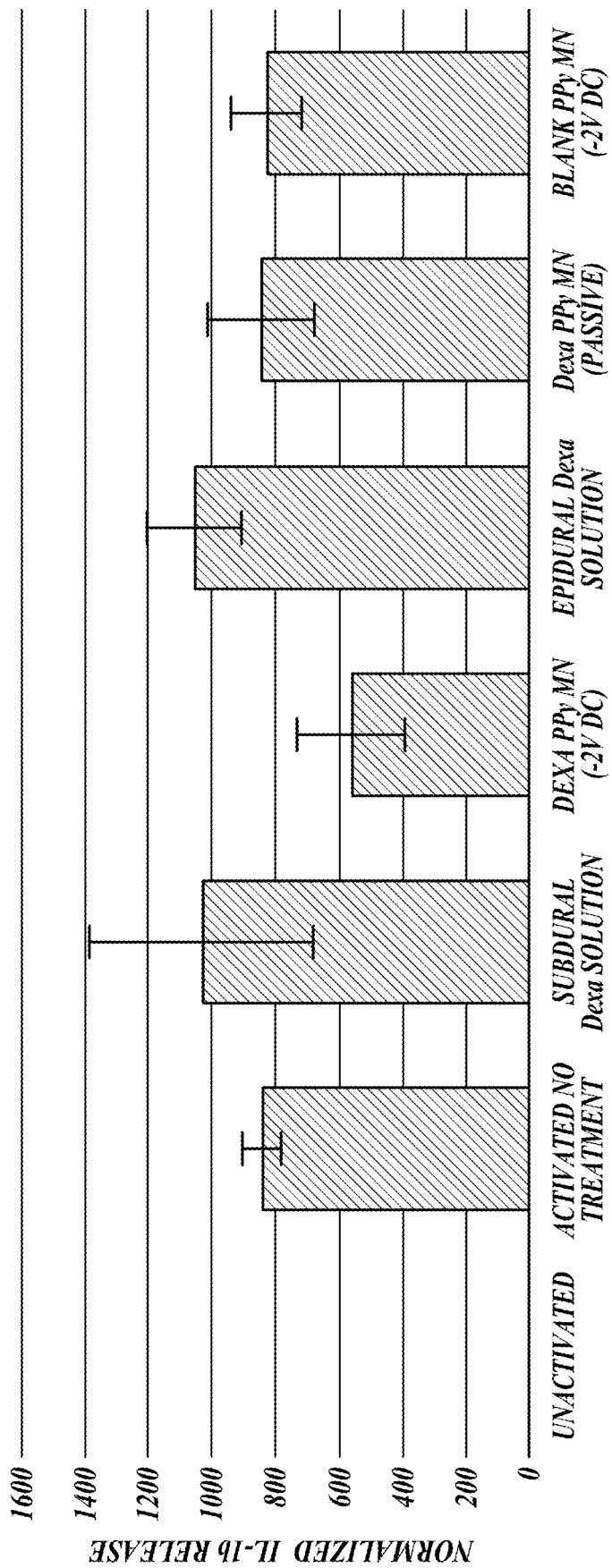
FIG. 11D is a bar graph of a neuroinflammation assay following transdural treatment that includes DC stimulation of an embodiment of a microneedle array of the present disclosure: IL-6 release normalized by the amount of viable cells quantified by MTS metabolism.
Figure 11E:
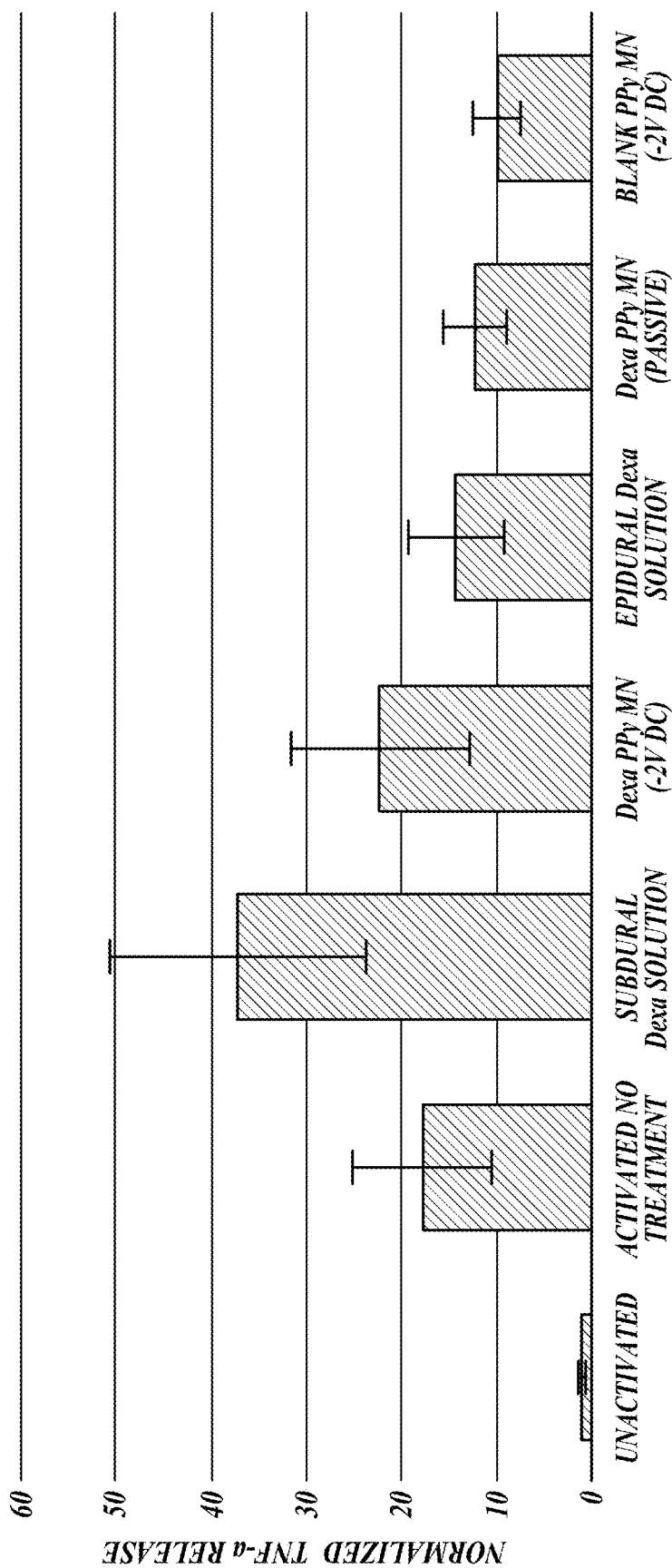
FIG. 11E is a bar graph of a neuroinflammation assay following transdural treatment that includes DC stimulation of an embodiment of a microneedle array of the present disclosure: TNF-α release normalized by the amount of viable cells quantified by MTS metabolism.

The release of pro-inflammatory cytokines did not experience similar patterns. The quantification of IL-1β, IL-6, and TNF-α show reduced total release in groups treated with DC stimulated Dexa PPy microneedles, but following normalization to cell viability (FIGS. 11C, 11D, 11E), the decrease was no longer observed.

CV Stimulated Release

The attenuation of neuroinflammation was similarly tested in CV stimulated Dexa PPy microneedles. Similar controls as previous were used, with the addition of a CV stimulated flat Dexa PPy electrode. Following the three day incubation, NO and pro-inflammatory cytokines IL-1β, IL-6, TNF-α, and MCP-1 were quantified using Griess and Luminex assays. Cell viability was again quantified using an MTS assay.

Figure 12A:
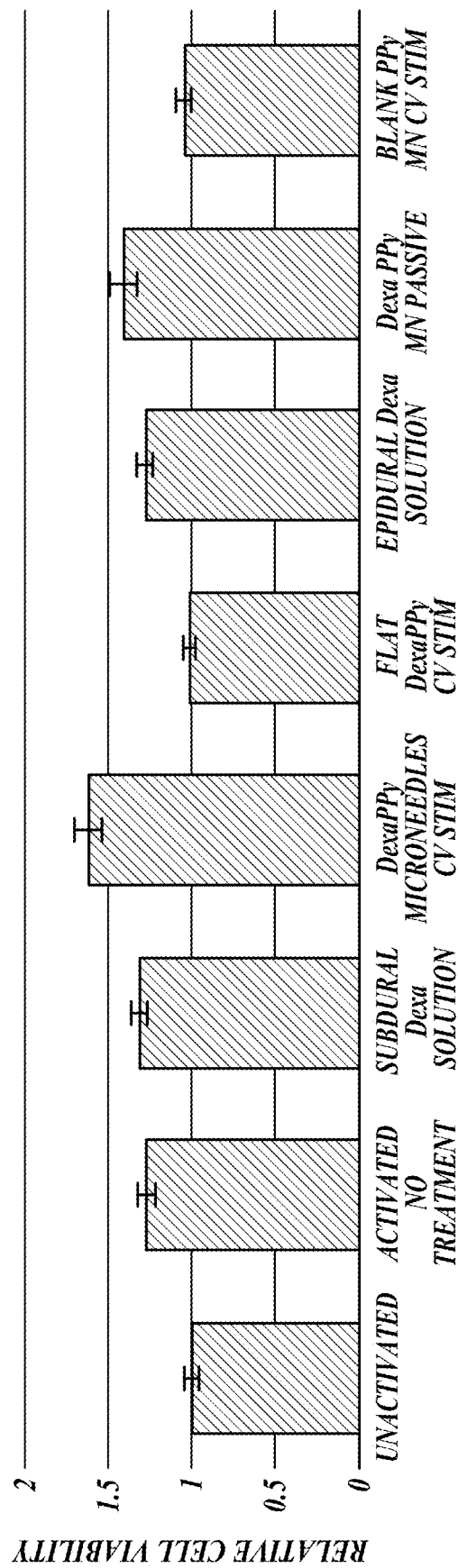
FIG. 12A is a bar graph of a neuroinflammation assay following transdural treatment that includes CV stimulation of an embodiment of a microneedle array of the present disclosure: MTS quantified relative cell viability in each treatment group.

MTS relative cell viability quantification (FIG. 12A) of CV stimulated Dexa PPy stimulated cells did not see the same decrease as previously seen in the DC stimulated treatment group. Instead, cell viability of the CV stimulated Dexa PPy microneedles group was increased compared to that of the controls. No groups in this experiment saw a decrease in cell viability, as measured by MTS metabolism, compared to that of unactivated cells.

Figure 12B:
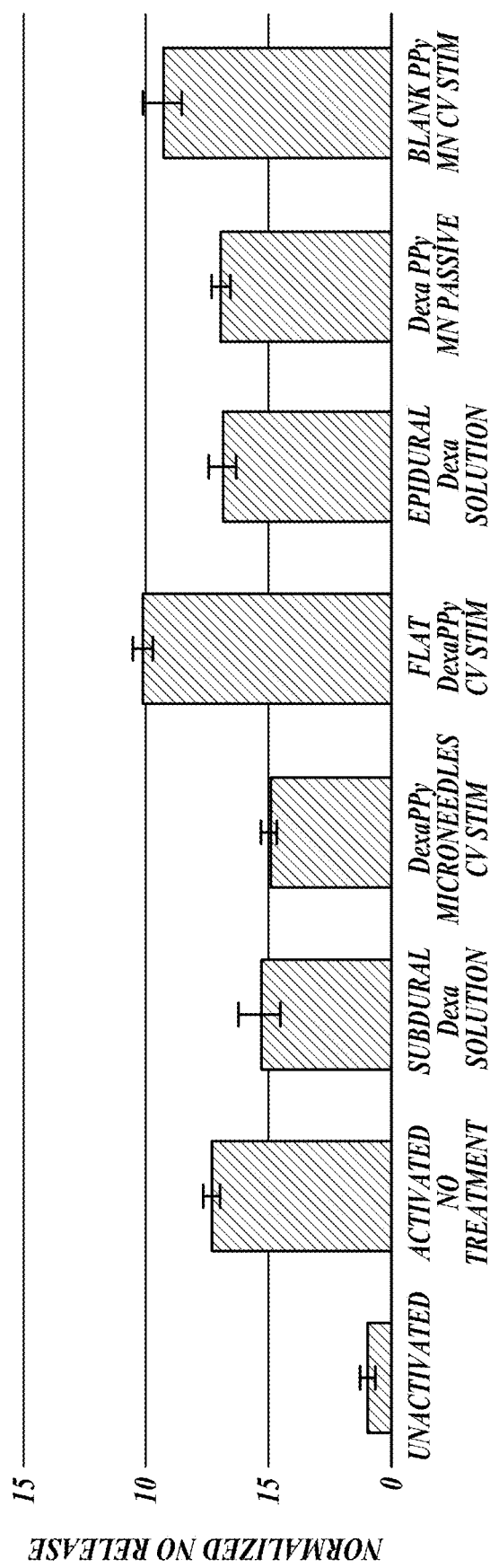
FIG. 12B is a bar graph of a neuroinflammation assay following transdural treatment that includes CV stimulation of an embodiment of a microneedle array of the present disclosure: NO release normalized by the amount of viable cells quantified by MTS metabolism.

Quantified release of inflammatory markers were then normalized to the amount of viable cells as measured using the MTS assay. NO release from the treated microglia, normalized for viable cells (FIG. 12B), saw a reduction in the CV stimulated Dexa PPy microneedles treatment group. Subdural Dexa solution treated microglia experienced a similar reduction in normalized NO release. Activated microglia treated with CV stimulated flat Dexa PPy, epidural Dexa solution, non-stimulated Dexa PPy microneedles, or CV stimulated blank PPy microneedles did not see similar reductions in NO release. These treatment groups had previously been demonstrated to result in no transdural Dexa release, which likely correspond to the lack of reduction in the neuroinflammation marker. Surprisingly, the groups of CV stimulated flat PPy and blank PPy microneedles were seen to result in a slight increase in NO release. This increase may indicate a mechanism of increases in inflammation as a result of the stimulation parameters, which in the CV stimulated Dexa PPy microneedles is reduced by dexamethasone treatment.

Figure 12C:
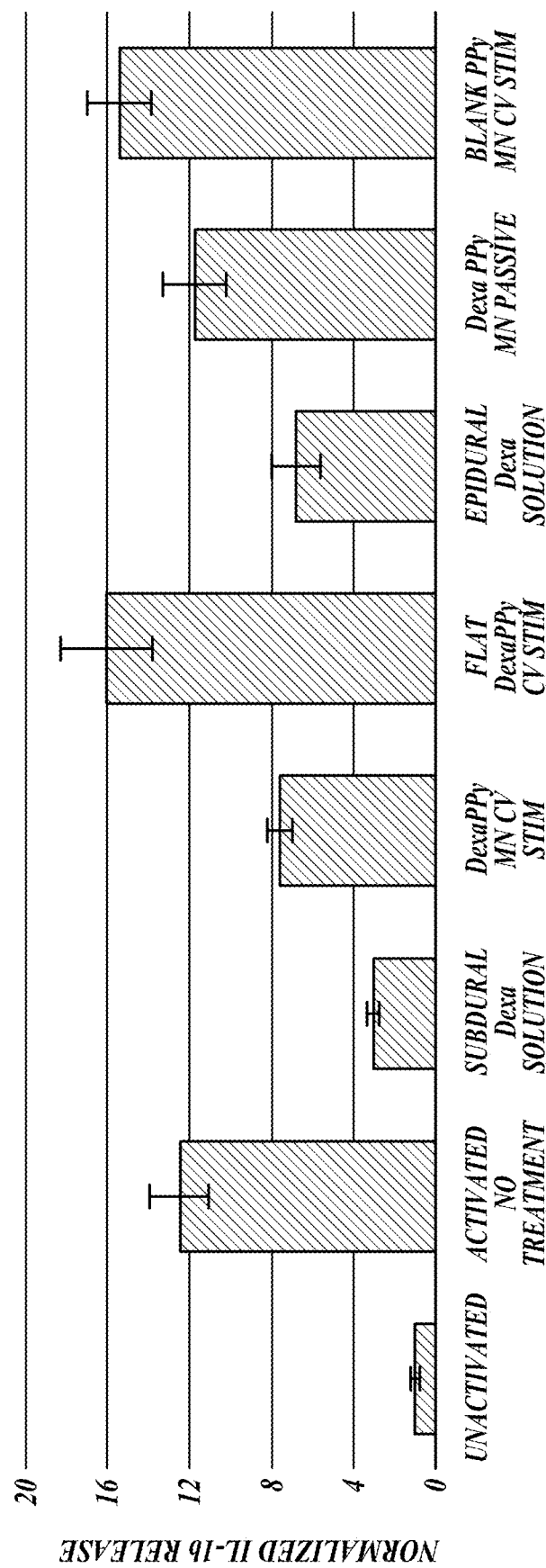
FIG. 12C is a bar graph of a neuroinflammation assay following transdural treatment that includes CV stimulation of an embodiment of a microneedle array of the present disclosure: IL-1β release normalized by the amount of viable cells quantified by MTS metabolism.
Figure 12D:
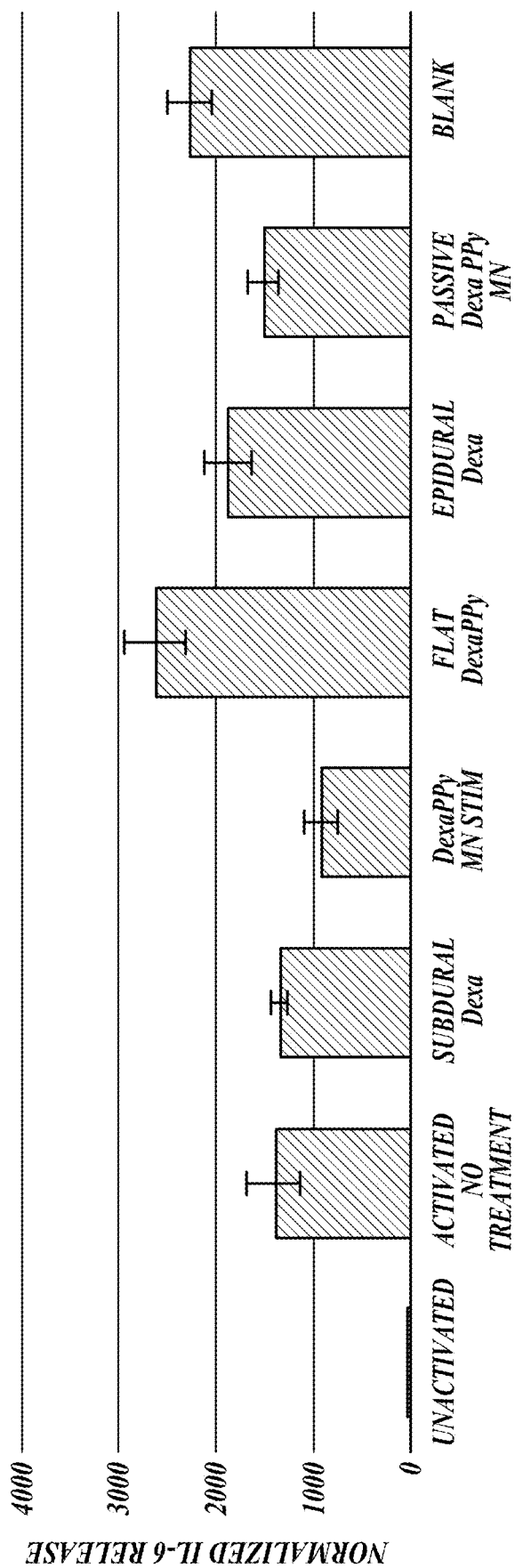
FIG. 12D is a bar graph of a neuroinflammation assay following transdural treatment that includes CV stimulation of an embodiment of a microneedle array of the present disclosure: IL-6 release normalized by the amount of viable cells quantified by MTS metabolism.
Figure 12E:
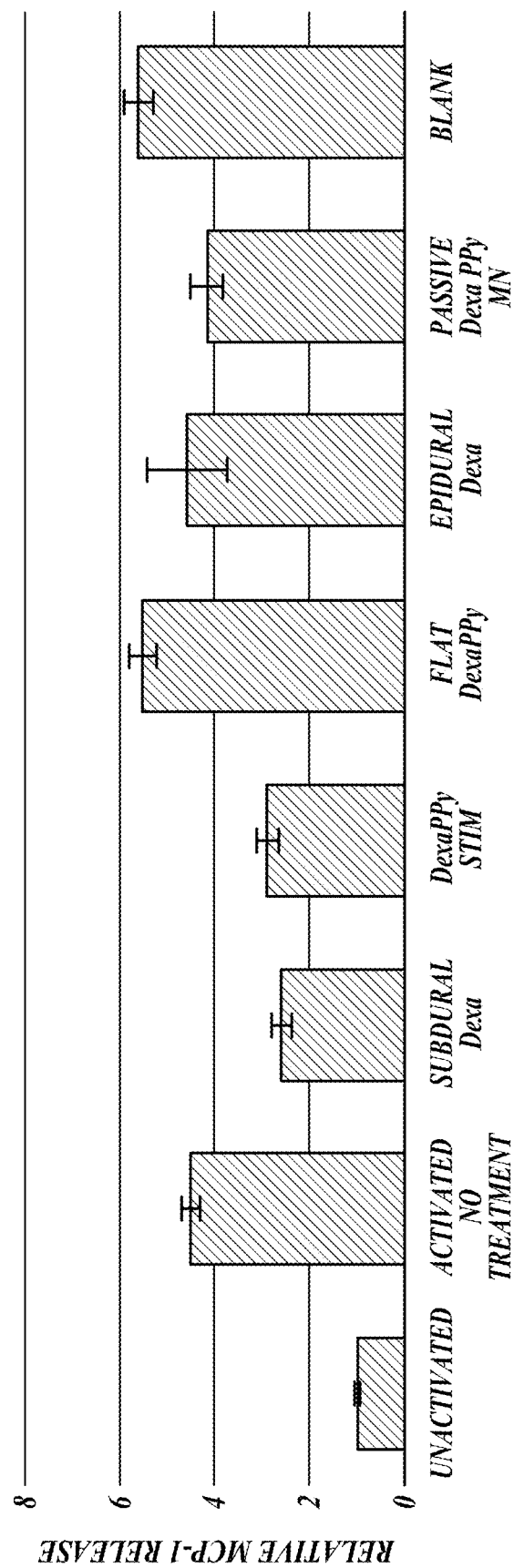
FIG. 12E is a bar graph of a neuroinflammation assay following transdural treatment that includes CV stimulation of an embodiment of a microneedle array of the present disclosure: MCP-1 release normalized by the amount of viable cells quantified by MTS metabolism.
Figure 12F:
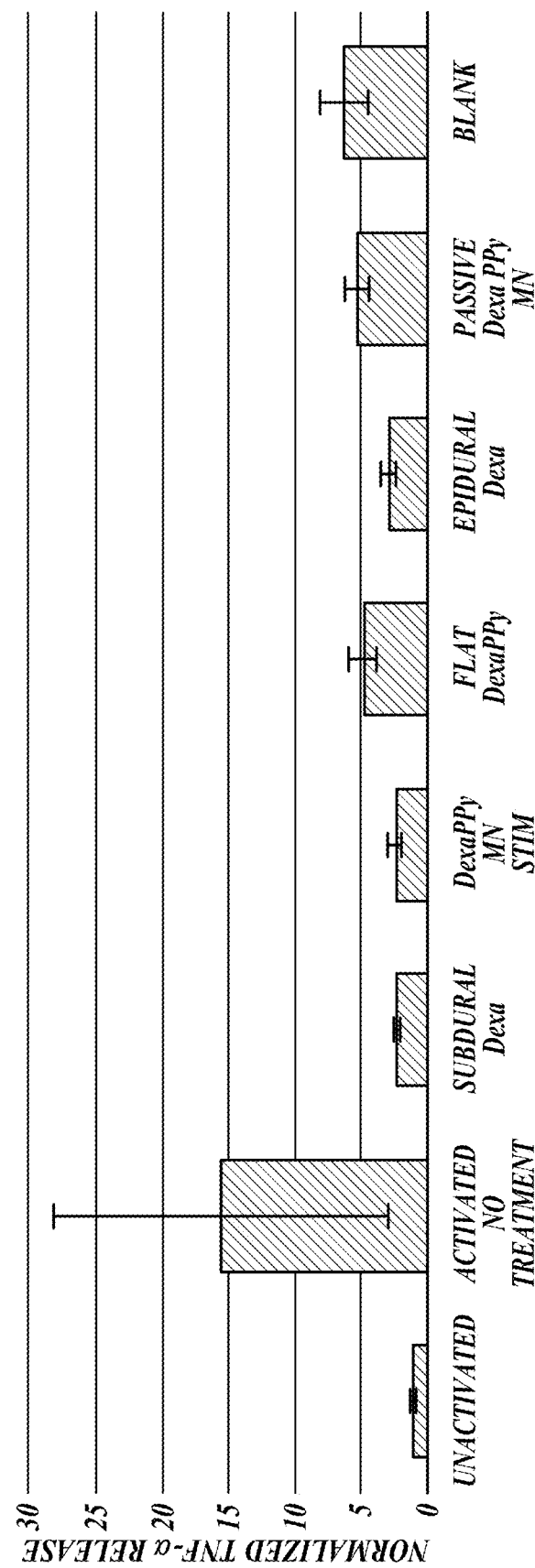
FIG. 12F is a bar graph of a neuroinflammation assay following transdural treatment that includes CV stimulation of an embodiment of a microneedle array of the present disclosure: TNF-α release normalized by the amount of viable cells quantified by MTS metabolism.

Normalized release of pro-inflammatory cytokines IL-1β, IL-6, and MCP-1 (FIGS. 12C, 12D, and 12E) show similar patterns of decrease from microglia treated with CV stimulated Dexa PPy microneedles (FIGS. 12C, 12D, 12E). IL-1β, IL-6, and TNF-α (FIG. 12F) saw a pattern of decrease in the CV stimulated Dexa PPy microneedles treated microglia. The release of MCP-1 display a similar pattern to that of NO. Treatment of CV stimulated Dexa PPy microneedles resulted in a greater decrease in the release of MCP-1, while controls of CV stimulated flat Dexa PPy, epidural Dexa solution, non-stimulated Dexa PPy microneedles, and CV stimulated blank PPy microneedles did not see the same decrease. The reduction of inflammatory cytokines, as well as NO, indicates that CV stimulated Dexa PPy microneedles can used transdurally to attenuate neuroinflammation.

Thus, the present Example shows that transdurally released Dexa from electrically stimulated Dexa PPy microneedles have the capability of transdural release of drugs that were unable to passively diffuse through the membrane. Use of the microneedles allowed subdural release of the drug with minimal damage to the dura, and minimal disruption in the subdural space. The release of Dexa on electrical stimulation additionally allowed the external control of drug release after the application of the microneedles. Application of transdural, electrically stimulated release from the microneedles to in vitro neuroinflammation show bioactivity of the released Dexa. CV stimulated release from the microneedles was not seen to cause significant cell death. Transdural release of Dexa from the PPy microneedles using CV stimulation could attenuate neuroinflammation, a mechanism of secondary spinal cord injury that may worsen the injury.

While this work uses dexamethasone phosphate to investigate transdural release from the PPy microneedles, a variety of pharmaceutical compounds can be loaded and released from conducting polymers, including protein therapeutics and neuroprotective compounds.

While illustrative embodiments have been illustrated and described, it will be appreciated that various changes can be made therein without departing from the spirit and scope of the disclosure.

The invention claimed is:

1. A method of delivering a therapeutic agent to a central nervous system, comprising:
providing a microneedle array comprising a plurality of microneedles, the plurality of microneedles comprising a conductive coating disposed thereon, wherein the conductive coating comprises the therapeutic agent and a conducting polymer;
implanting the microneedle array in a dura mater of a subject in need thereof, wherein the microneedle array pierces the dura mater; and
applying an electrical stimulus to the microneedle array to provide a controlled release of the therapeutic agent from the conductive coating, across the dura mater, to the central nervous system of the subject.

2. The method of claim 1, wherein the conducting polymer is selected from polypyrrole, polythiophene, polyaniline, poly(3,4-ethylenedioxythiophene), substituted derivatives thereof, and any combination thereof.

3. The method of claim 1, wherein the therapeutic agent is selected from an anti-inflammatory agent, a serotonin agonist, a neurotrophic factor, and any combination thereof.

4. The method of claim 1, wherein the therapeutic agent is selected from dexamethasone, methylprednisolone, triamcinolone, IL-10, quipazine, riluzole, a nerve growth factor, a brain-derived neurotrophic factor, a neuroregenerative agent, a neuroprotective agent, a chemotherapeutic agent, a bone-growth stimulating agent, a pharmaceutically acceptable prodrug thereof, a pharmaceutically acceptable salt thereof, and any combination thereof.

5. The method of claim 1, wherein the electrical stimulus comprises application of a voltage of from −10V to +10V for a duration of from 1 second to 72 hours.

6. The method of claim 1, wherein the therapeutic agent is dispersed in the conducting polymer.

7. The method of claim 1, wherein at least a portion of microneedles of the plurality of microneedles has a height of from 100 µm to 3000 µm and a base diameter of 25 µm to 500 µm.

8. The method of claim 1, wherein the dura mater is located in a spinal cord of the subject.

9. The method of claim 1, wherein the dura mater is located in a brain of the subject.

* * * * *